(12) United States Patent
Cronenberg et al.

(10) Patent No.: US 12,102,805 B2
(45) Date of Patent: *Oct. 1, 2024

(54) INJECTION PEN WITH DIAL BACK AND LAST DOSE CONTROL

(71) Applicant: Becton, Dickinson and Company, Franklin Lakes, NJ (US)

(72) Inventors: Richard E. Cronenberg, Mahwah, NJ (US); Michael Quinn, East Hanover, NJ (US); Haiming Wu, Weston, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 144 days.

This patent is subject to a terminal disclaimer.

(21) Appl. No.: 17/194,123

(22) Filed: Mar. 5, 2021

(65) Prior Publication Data

US 2021/0187203 A1 Jun. 24, 2021

Related U.S. Application Data

(62) Division of application No. 15/669,349, filed on Aug. 4, 2017, now Pat. No. 10,940,269, which is a division
(Continued)

(51) Int. Cl.
*A61M 5/315* (2006.01)
*A61M 5/24* (2006.01)
(Continued)

(52) U.S. Cl.
CPC .... *A61M 5/31548* (2013.01); *A61M 5/31535* (2013.01); *A61M 5/31541* (2013.01);
(Continued)

(58) Field of Classification Search
CPC .......... A61M 5/31548; A61M 5/31535; A61M 5/31541; A61M 5/31551; A61M 5/3156;
(Continued)

(56) References Cited

U.S. PATENT DOCUMENTS 5,725,508 A 3/1998 Chanoch
6,235,004 B1 5/2001 Steenfeldt-Jenen
(Continued)

FOREIGN PATENT DOCUMENTS

DE 102007054019 A1 5/2009
EP 1250167 B1 7/2005
(Continued)

*Primary Examiner* — Robert J Utama
*Assistant Examiner* — Hamza A Darb
(74) *Attorney, Agent, or Firm* — Dickinson Wright PLLC

(57) ABSTRACT

A medication injection pen comprises a dose set knob rotatable with respect to a housing to set a desired injection dose. The dose set knob comprises at least one internal thread. A leadscrew includes a thread element for advancing in a first direction via a corresponding thread engagement. A driver is rotationally fixed to the leadscrew and is rotatable in a first direction to rotate and advance the leadscrew in the first direction. The setback member is rotationally fixed to the driver. The dose stop member is rotationally coupled to the setback member and is axially movable relative to the dose set knob when the dose set knob is rotated relative to the setback member. Axial movement of the dose stop member limits the user from setting a dose that is greater than an injectable volume of medication remaining in a cartridge.

10 Claims, 38 Drawing Sheets

Related U.S. Application Data of application No. 13/261,300, filed as application No. PCT/US2010/003059 on Nov. 30, 2010, now Pat. No. 9,757,525.

(60) Provisional application No. 61/351,465, filed on Jun. 4, 2010, provisional application No. 61/265,562, filed on Dec. 1, 2009.

(51) Int. Cl.
*A61M 5/32* (2006.01)
*A61M 5/34* (2006.01)

(52) U.S. Cl.
CPC ...... *A61M 5/31551* (2013.01); *A61M 5/3156* (2013.01); *A61M 5/31563* (2013.01); *A61M 5/31585* (2013.01); *A61M 5/31595* (2013.01); *A61M 5/24* (2013.01); *A61M 2005/2407* (2013.01); *A61M 5/2466* (2013.01); *A61M 2005/2488* (2013.01); *A61M 2005/2492* (2013.01); *A61M 5/31543* (2013.01); *A61M 5/3157* (2013.01); *A61M 5/31573* (2013.01); *A61M 5/31575* (2013.01); *A61M 5/3202* (2013.01); *A61M 5/347* (2013.01); *A61M 2205/581* (2013.01)

(58) Field of Classification Search
CPC .......... A61M 5/31563; A61M 5/31585; A61M 5/31595; A61M 5/24; A61M 5/2466; A61M 5/31543; A61M 5/3157; A61M 5/31573; A61M 5/31575; A61M 5/3202; A61M 5/347; A61M 2005/2407; A61M 2005/2488; A61M 2005/2492; A61M 2205/581; A61M 5/31556

See application file for complete search history.

(56) References Cited

U.S. PATENT DOCUMENTS

| | | |
|---|---|---|
| 6,248,095 B1 | 6/2001 | Giambattista |
| 6,936,032 B1 | 8/2005 | Bush, Jr. |
| 7,195,616 B2 | 3/2007 | Diller |
| 7,195,623 B2 | 3/2007 | Burroughs |
| 7,241,278 B2 | 7/2007 | Moller |
| 9,757,525 B2 * | 9/2017 | Cronenberg ...... A61M 5/31595 |
| 2004/0097883 A1 | 5/2004 | Roe |
| 2004/0127858 A1 | 7/2004 | Bendek et al. |
| 2004/0199117 A1 | 10/2004 | Giambattista |
| 2005/0165363 A1 | 7/2005 | Judson et al. |
| 2005/0261634 A1 | 11/2005 | Karlsson |
| 2006/0206057 A1 * | 9/2006 | DeRuntz ........... A61M 5/31558 604/224 |
| 2007/0167921 A1 | 7/2007 | Burren |
| 2009/0054851 A1 | 2/2009 | Radmer et al. |
| 2021/0187202 A1 * | 6/2021 | Cronenberg ........ A61M 5/3156 |

FOREIGN PATENT DOCUMENTS

| | | |
|---|---|---|
| JP | 2002501790 A | 1/2002 |
| JP | 2004510554 A | 4/2004 |
| JP | 2006519075 A | 8/2006 |
| JP | 2007502146 A | 2/2007 |
| JP | 2008528144 A | 7/2008 |
| JP | 2008529625 A | 8/2008 |
| JP | 2008229346 A | 10/2008 |
| WO | 2006084876 A1 | 8/2006 |
| WO | 2007017052 A1 | 2/2007 |
| WO | 2008003560 A1 | 1/2008 |

* cited by examiner

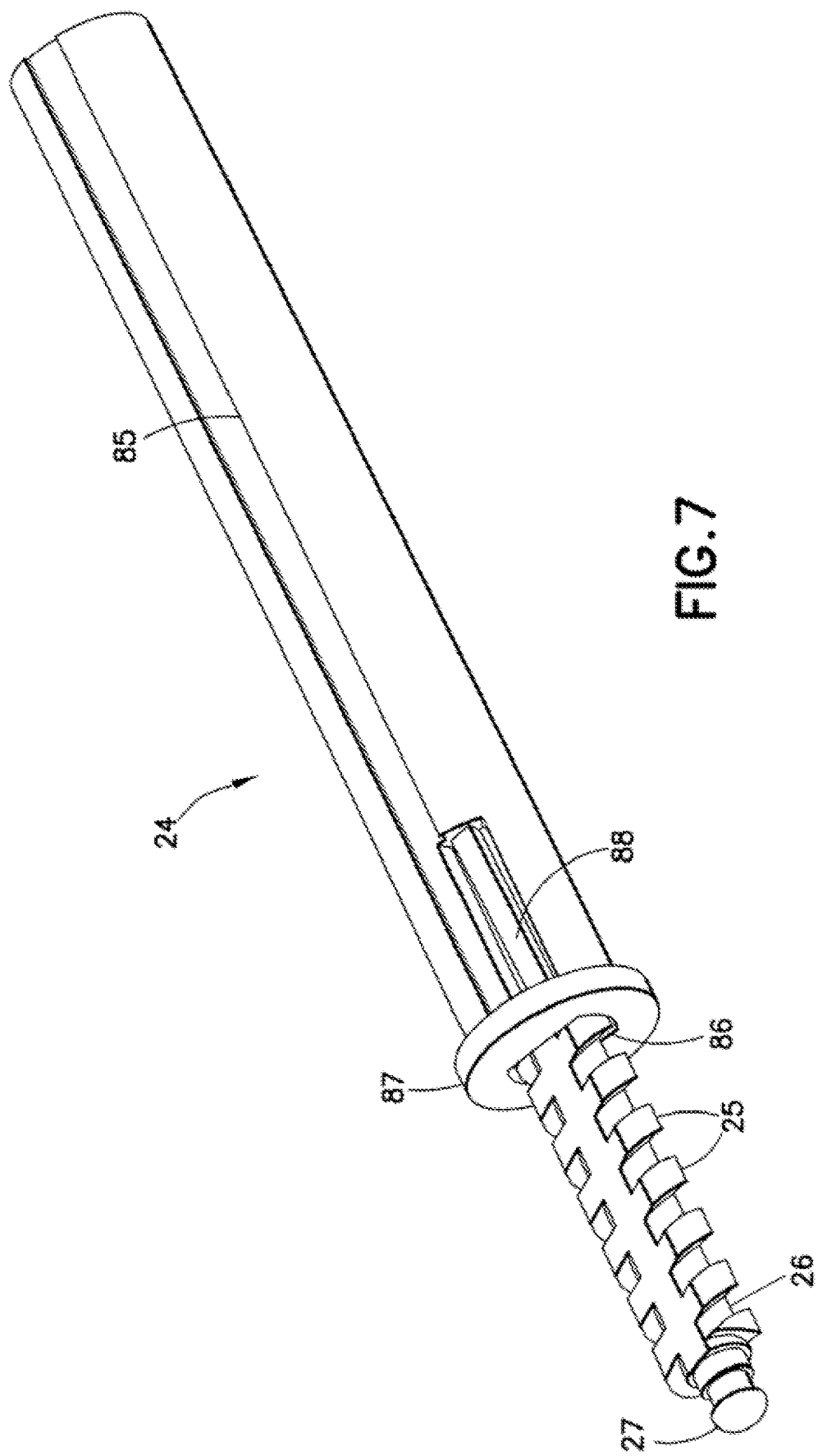

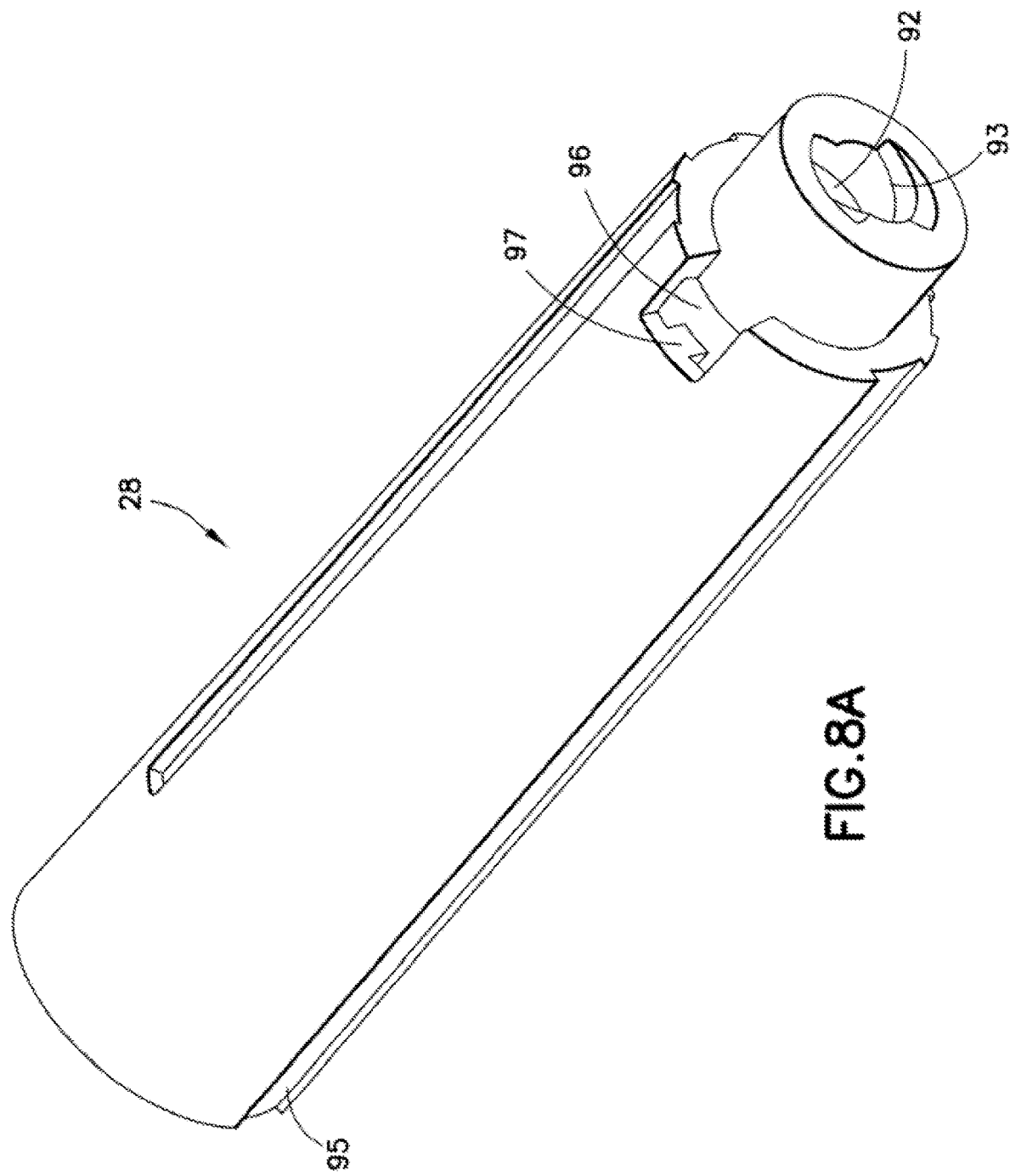

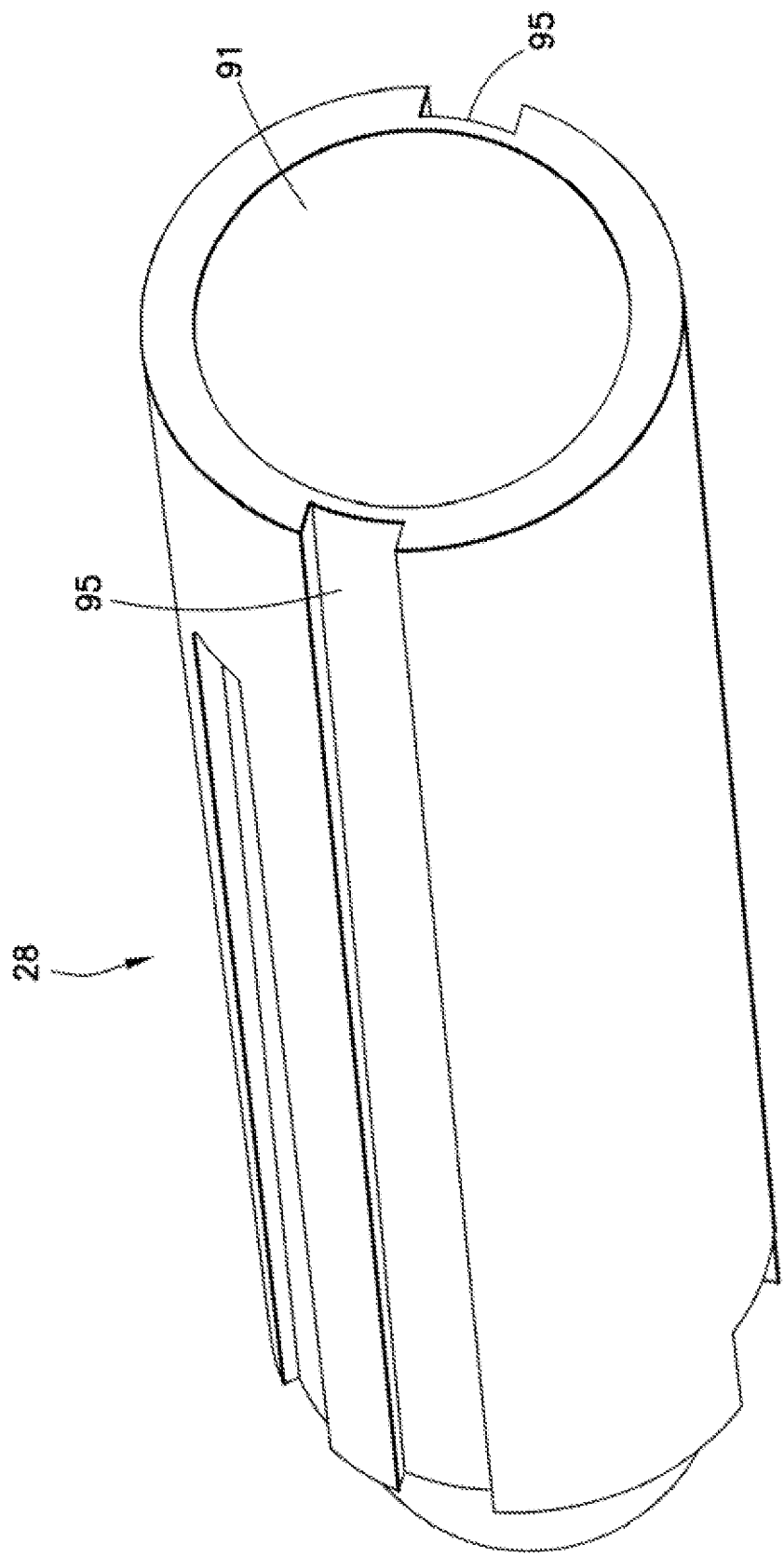

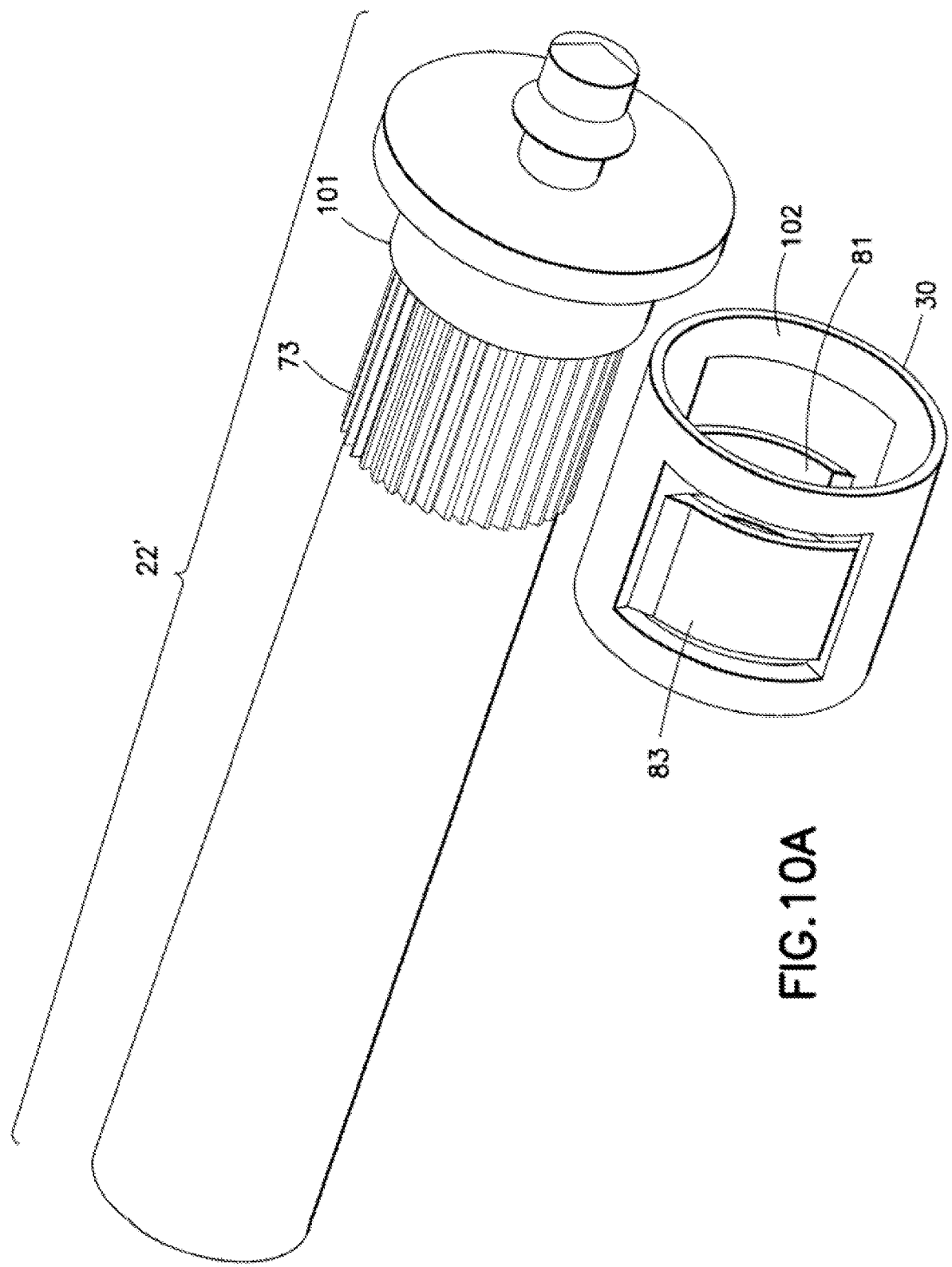

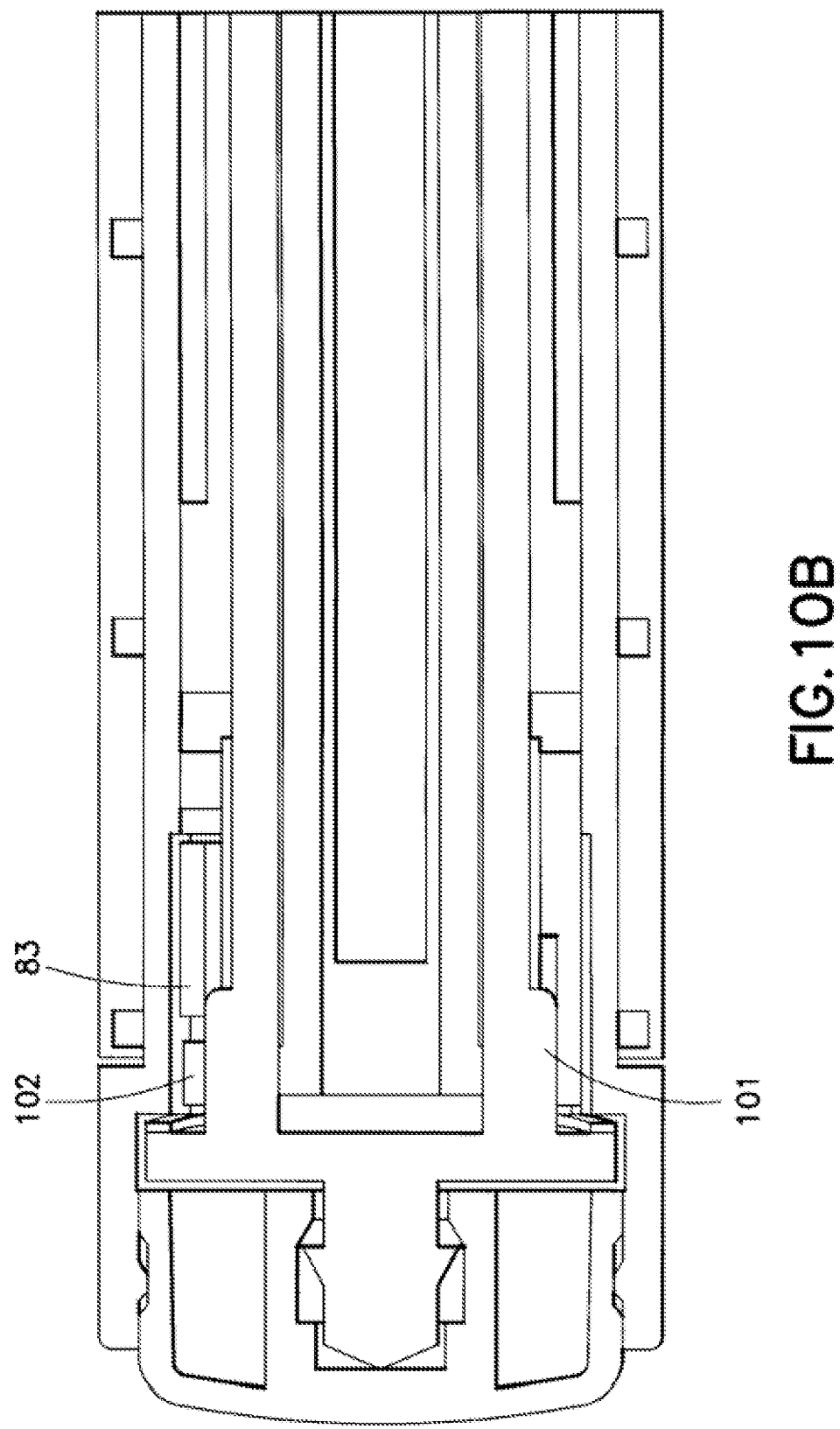

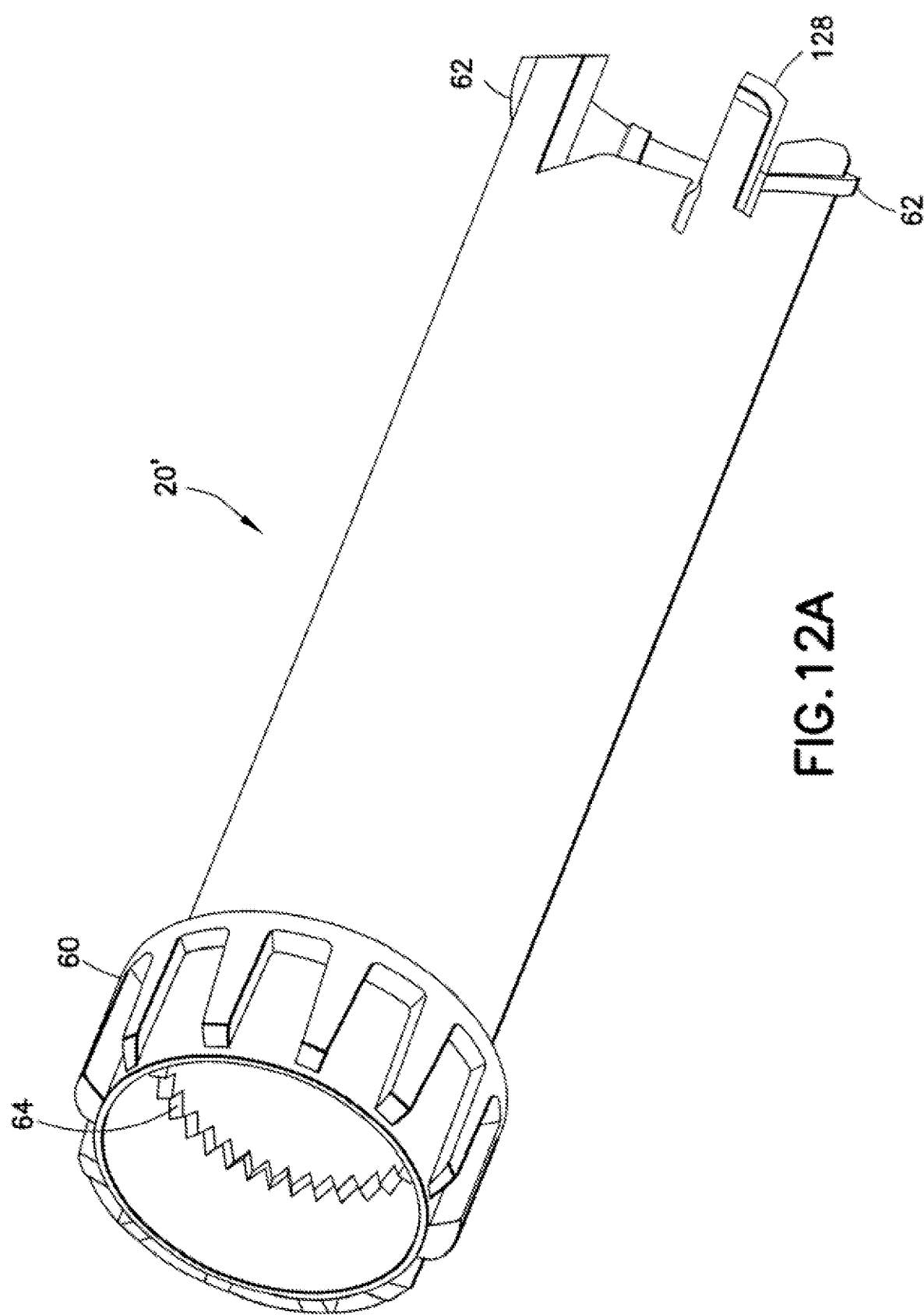

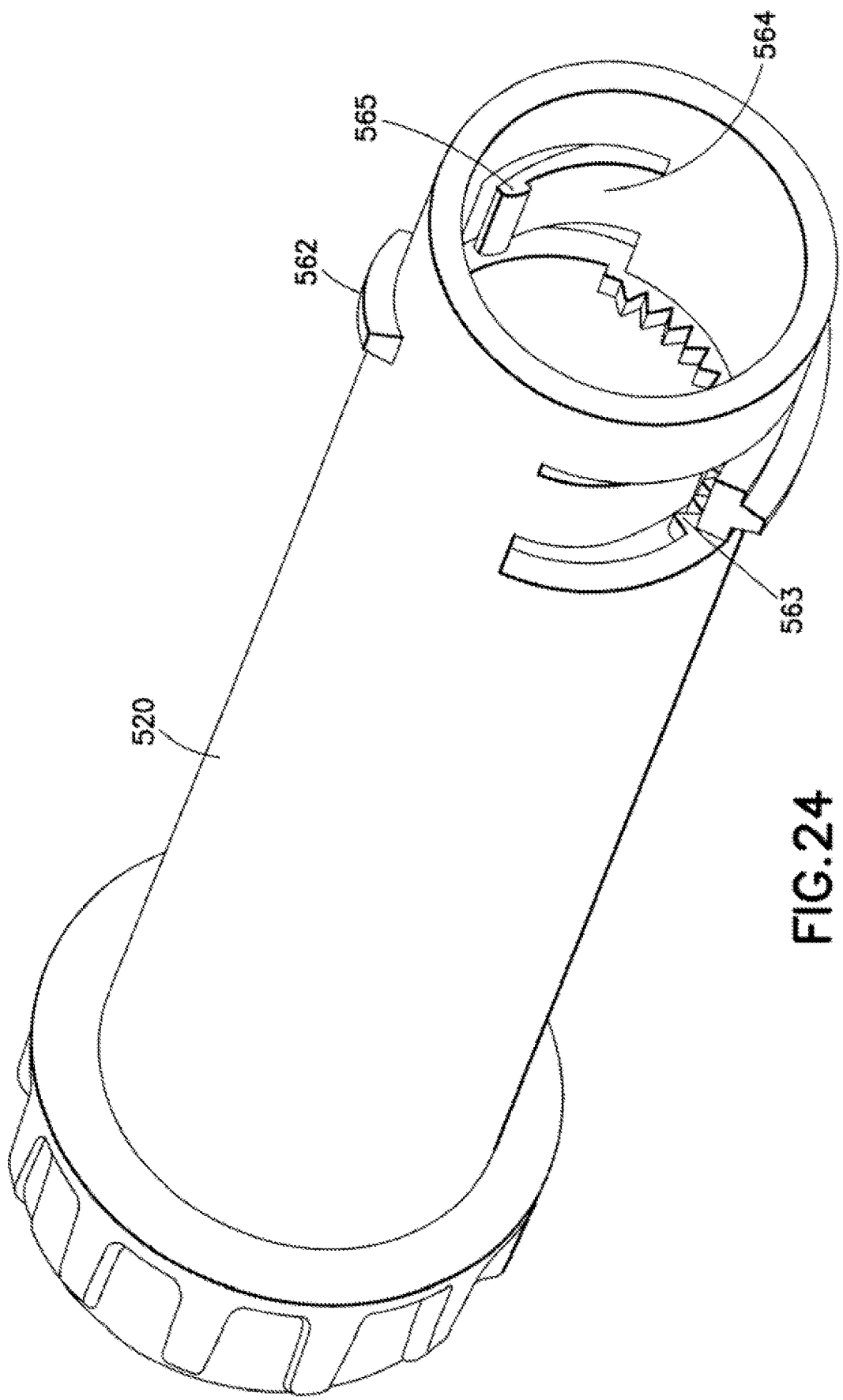

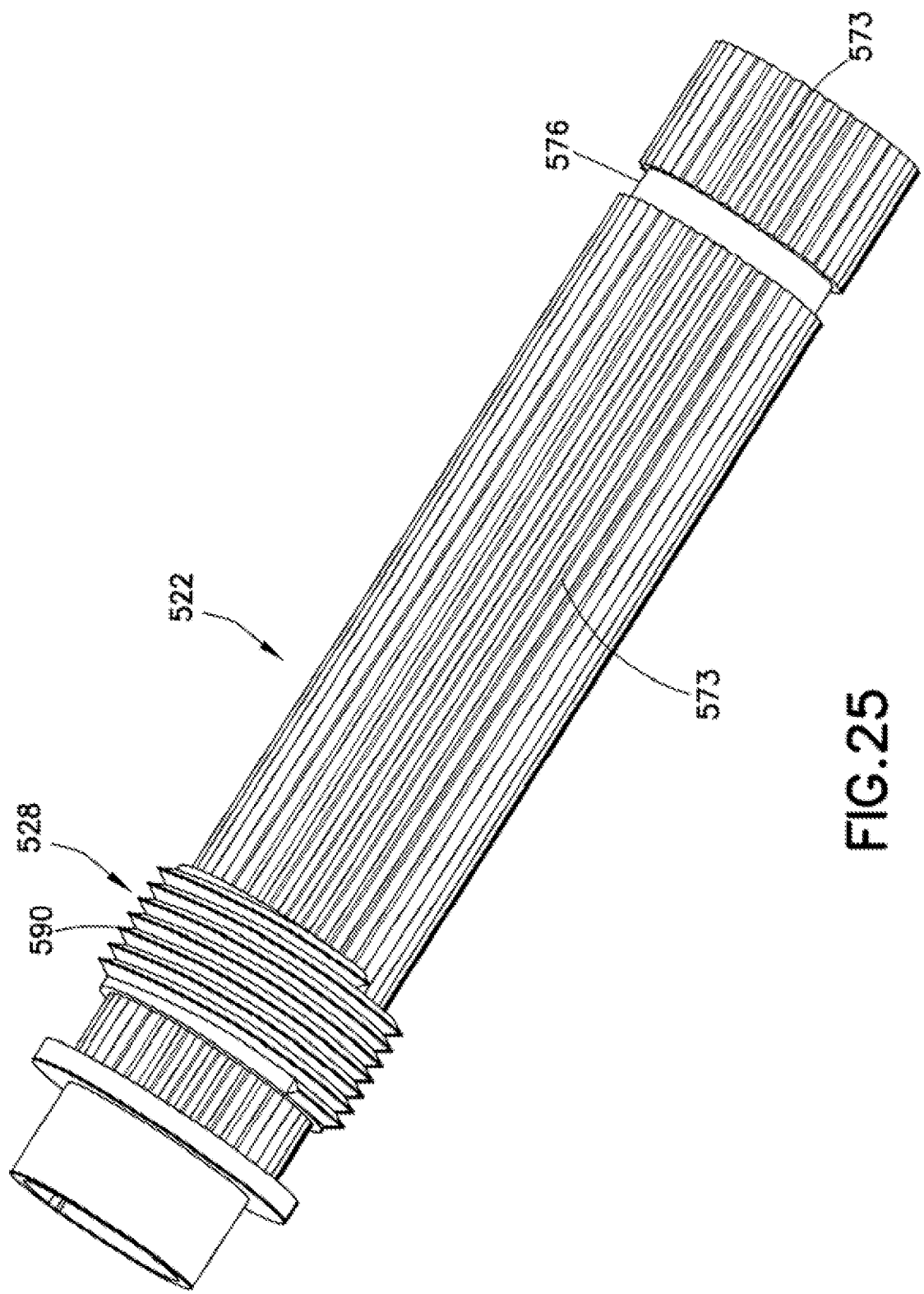

INJECTION PEN WITH DIAL BACK AND LAST DOSE CONTROL

RELATED APPLICATIONS

This application is a division of U.S. Nonprovisional application Ser. No. 15/669,349, filed on Aug. 4, 2017, now U.S. Pat. No. 10,940,269B2, issued Mar. 9, 2021, which is a division of U.S. Nonprovisional application Ser. No. 13/261,300, filed on Jul. 27, 2012, now U.S. Pat. No. 9,757,525B2, issued Sep. 12, 2017, which is a U.S. national stage application under 35 U.S.C. § 371 of International Application No. PCT/US10/003059, filed Nov. 30, 2010, which claims the benefit of U.S. Provisional Patent Applications Ser. No. 61/265,562, filed on Dec. 1, 2009, and Ser. No. 61/351,465, filed on Jun. 4, 2010, each of which is incorporated herein in its entirety.

FIELD OF THE INVENTION

The present application relates to multi-dose medication injection pen devices with improved functionality, including improved dial-back of a set dose, and improved last dose control.

BACKGROUND OF THE INVENTION

Various medication injection pen devices are known in the prior art. These prior art devices sometimes include features for enabling a user to correct a dose that has been set too large, which may be referred to as "dial back". Another feature that may be provided by some of the prior art devices is the ability to control a last dose of a medication cartridge such that a user cannot set a dose greater than the remaining amount of medication in the cartridge. This feature is referred to as last dose control or last dose management. Both of these features are desired by users of such pen devices; however, the prior art devices do not satisfactorily meet these needs. Many prior art devices may provide one of these features, but not both. Further, many of the prior art devices require additional steps for performing dial back, which are cumbersome and not intuitive to the user. Thus, there is a need in the art to provide improved functionality of dial back and last dose control mechanisms together in a medication injection pen.

SUMMARY OF EMBODIMENTS OF THE INVENTION

Exemplary embodiments of the present invention address at least the above problems and/or disadvantages and provide at least the advantages described below.

Accordingly, first exemplary embodiment of the present invention provides a medication injection pen comprising a housing, for housing a dose set knob, a leadscrew, a driver, a setback member, and a dose stop member. The dose set knob is rotatable with respect to said housing to set a desired injection dose, and comprises at least one internal thread. The leadscrew includes a thread element by which it is advanceable in a first direction via a corresponding thread engagement, said first direction being that which expels medication from a cartridge. The driver is rotationally fixed to said leadscrew for preventing relative rotation therebetween, said driver being rotatable in a first direction to rotate and advance said leadscrew in said first direction. The setback member is rotationally fixed to said driver for preventing relative rotation therebetween. The dose stop member is rotationally fixed to said setback member and comprises an external thread in threaded engagement with said internal thread of said dose set knob, said dose stop member being axially movable relative to said dose set knob when said dose set knob is rotated relative to said setback member, and wherein axial movement of said dose stop member limits the user from setting a dose that is greater than an injectable volume of medication remaining in the cartridge.

According to another exemplary embodiment of the present invention a medication injection pen is provided comprising a housing, for housing a dose set knob, a leadscrew, a driver, a setback member, and a dose stop member. The dose set knob is rotatable with respect to said housing to set a desired injection dose. The leadscrew includes a thread element by which it is advanceable in a first direction via a corresponding thread engagement, said first direction being that which expels medication from a cartridge. The driver is rotationally fixed to said leadscrew for preventing relative rotation therebetween, said driver being rotatable in a first direction to rotate and advance said leadscrew in said first direction. The setback member is rotationally fixed to said driver for preventing relative rotation therebetween, and is provided with an external thread thereon. The dose stop member is rotationally fixed to said dose set knob and comprises an internal thread in threaded engagement with said external thread of said setback member, said dose stop member being axially movable relative to said dose set knob when said dose set knob is rotated relative to said setback member, and wherein axial movement of said dose stop member limits a user from setting a dose that is greater than an injectable volume of medication remaining in the cartridge.

According to yet another exemplary embodiment of the present invention a medication injection pen is provided comprising a housing, for housing a dose set knob, a leadscrew, a driver, a setback member, and a dose stop member. The dose set knob is rotatable with respect to said housing to set a desired injection dose. The leadscrew includes a thread element by which it is advanceable in a first direction via a corresponding thread engagement, said first direction being that which expels medication from a cartridge. The driver is rotationally fixed to said leadscrew for preventing relative rotation therebetween, said driver being rotatable in a first direction to rotate and advance said leadscrew in said first direction. The setback member is rotationally fixed to said driver for preventing relative rotation therebetween. The dose stop member is rotationally fixed to said dose set knob and comprises an internal thread in threaded engagement with said thread of said leadscrew, said dose stop member being axially movable relative to said dose set knob when said dose set knob is rotated relative to said setback member, and wherein axial movement of said dose stop member limits a user from setting a dose that is greater than an injectable volume of medication remaining in the cartridge.

According to yet another exemplary embodiment of the present invention a medication injection pen is provided comprising a housing, for housing a dose set knob, a leadscrew, a driver, a setback member, and a click element. The dose set knob is rotatable with respect to said housing to set a desired injection dose. The leadscrew includes a thread element by which it is advanceable in a first direction via a corresponding thread engagement, said first direction being that which expels medication from a cartridge. The driver is rotationally fixed to said leadscrew for preventing relative rotation therebetween, said driver being rotatable in a first direction to rotate and advance said leadscrew in said first direction. The setback member is rotationally fixed to said driver for preventing relative rotation therebetween. The click element is positioned between said dose set knob and said setback member, said click element comprising a first arm member engaging an internal surface of said dose set knob, and a second arm member engaging an external surface of said setback member, wherein one of the said first and second arms produces an audible signal when said dose set knob is rotated with respect to said housing.

According to yet another exemplary embodiment of the present invention a medication injection pen is provided comprising a housing, for housing a dose set knob, a leadscrew, a driver, and a setback member. The dose set knob is rotatable with respect to said housing to set a desired injection dose. The leadscrew includes a thread element by which it is advanceable in a first direction via a corresponding thread engagement, said first direction being that which expels medication from a cartridge. The driver is rotationally fixed to said leadscrew for preventing relative rotation therebetween, said driver being rotatable in a first direction to rotate and advance said leadscrew in said first direction. The setback member is rotationally fixed to said driver for preventing relative rotation therebetween. The housing further comprises a flexible protrusion provided on a surface within said housing, and the dose set knob further comprises a flexible tab element which engages said protrusion to produce an audible signal upon completion of injection of a set dose.

Additional objects, advantages and salient features of exemplary embodiments of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which:

FIG. 7 depicts a view of a driver and leadscrew arrangement provided in a medication injection pen according to the first exemplary embodiment of the present invention;

FIGS. 8A and 8B depict views of a dose stop member provided in a medication injection pen according to the first exemplary embodiment of the present invention:

FIGS. 10A and 10B depict views of an alternative injection coupling mechanism provided in a medication injection pen according to the first exemplary embodiment of the present invention:

FIGS. 12A-12E depict views of an end-of-injection click mechanism in a medication injection pen according to the first exemplary embodiment of the present invention;

FIGS. 14A and 148 depict views of an additional mechanism for reducing friction between components in a medication injection pen according to the first exemplary embodiment of the present invention;

FIG. 24 depicts a view of a dose set knob provided in a medication injection pen according to the third exemplary embodiment of the present invention: and FIG. 25 depicts a view of a setback member provided in a medication injection pen according to the third exemplary embodiment of the present invention.

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the present disclosure with reference to the accompanying drawing figures. Accordingly, those of ordinary skill in the art will recognize that various changes to and modifications of the exemplary embodiments described herein can be made without departing from the scope and spirit of the claimed invention. Also, descriptions of well-known functions and constructions are omitted for clarity and conciseness.

Figure 1:
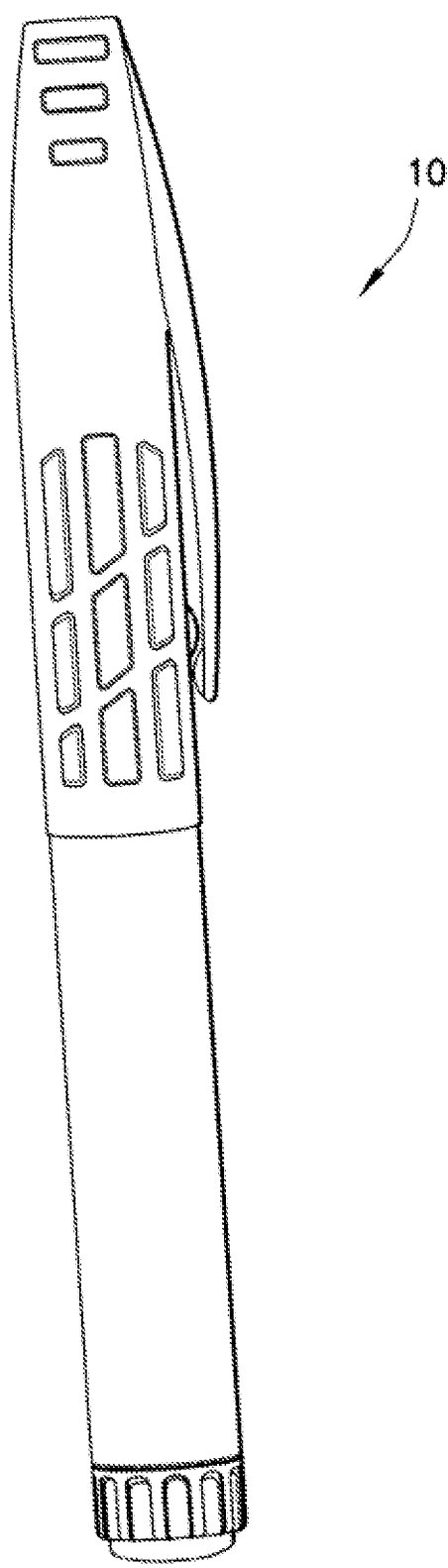
FIG. 1 depicts a medication injection pen according to an exemplary embodiment of the present invention.

With reference to the drawing figures, particularly FIG. 1, a medication injection pen is shown and generally designated with the reference numeral 10. The medication injection pen 10 may be used for the administration of various medications, preferably liquid in nature, including but not limited to insulin and human growth hormone. The term "medication" is used in an illustrative and non-limiting manner to refer to any substance that may be injected into a patient for any purpose. The medication injection pen 10 is provided for administering multiple injections, the dose or volume of which may be set by the user and may vary for each injection. Exemplary embodiments of medication injection pen 10 of the present disclosure may be either disposable or reusable when the supply of medication therein has been exhausted.

Figure 2A:
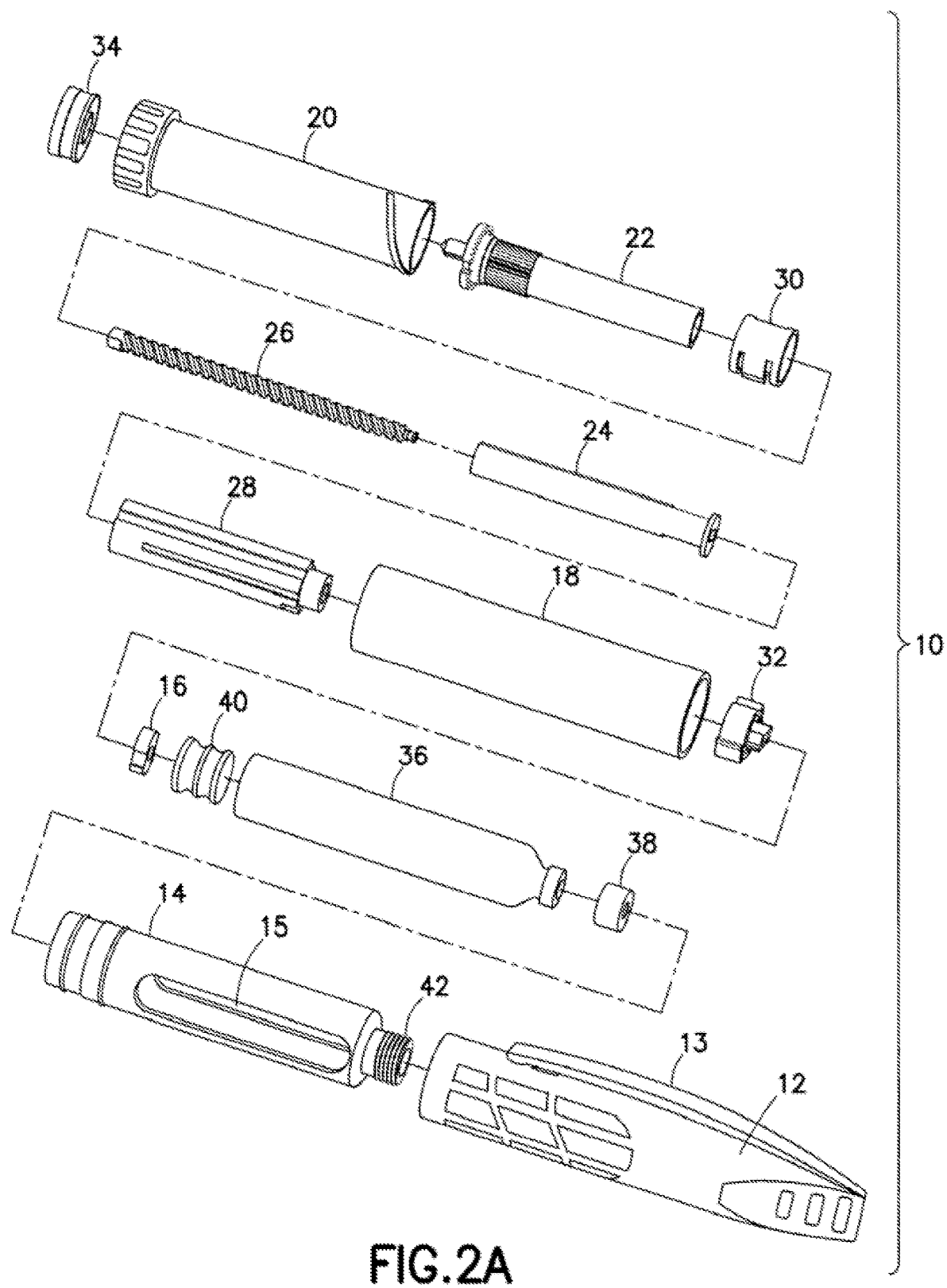
FIGS. 2A and 2B depict unassembled and assembled cross-sectional views, respectively, of exemplary components provided in a medication injection pen according to a first exemplary embodiment of the present invention.
Figure 2B:
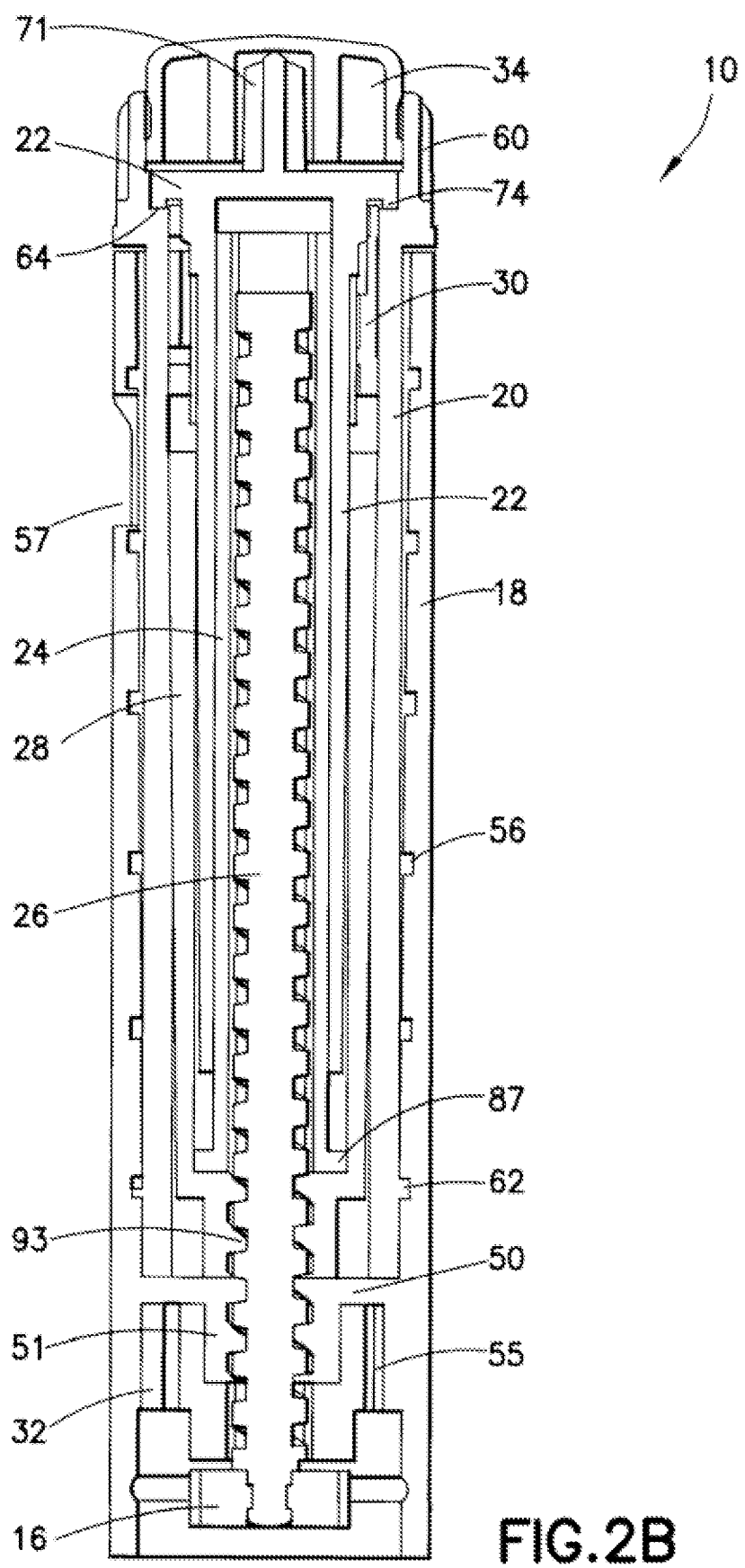

With reference to FIGS. 2A and 2B, in an exemplary embodiment, the medication injection pen 10 generally includes a cap 12, a cartridge holder 14, a spinner 16, a body 18, a dose knob 20, a setback member 22, a driver member 24, a leadscrew 26, a dose stop member 28, a bi-directional click element 30, a leadscrew brake 32, and a push button 34.

The cartridge holder 14 is formed to accommodate a medication cartridge 36, which may be of any conventional design. By way of non-limiting example, the cartridge 36 may include an elastomeric septum 38 at a distal end thereof, and an open proximal end 37 which exposes a slidable plunger 40. A medication is contained within the cartridge 36 between the septum 38 and the plunger 40. As will be described in more detail below, the spinner 16 is configured to engage the plunger 40 and force a distal movement thereof to expel the medication from the cartridge 36. The spinner 16 includes an aperture formed to snap fit or otherwise engage a distal end bead portion 27 (FIG. 7) of leadscrew 26 in mounting the spinner 16 onto the leadscrew 26. A standard pen needle 11 (FIG. 2C) is used to administer medication from the medication injection pen 10. The needle is a double-ended cannula 5 which is threadedly mounted onto threads 42 of the cartridge holder 14, as is well known in the art. One end of the cannula 5 is exposed for insertion into a patient, while the second end of the cannula is disposed to pierce the septum 38 of the cartridge 36. After administration of a set dose, the needle 11 may be removed, in which case, the septum 38 may be self-sealing. The cap 12 is formed to releasably mount onto the cartridge holder 14, such as with a snap in or other releasable engagement, to limit contamination of the septum 38 and the surrounding portions of the cartridge holder 14. A resilient holding arm 13 may extend from the cap 12 to provide a holding force for retaining the injection pen 10 in the user's pocket, purse, or carrying case. One or more windows 15 may also be provided in the cartridge holder 14 to give a visual indication of the medication volume remaining in the cartridge 36.

Figure 2C:
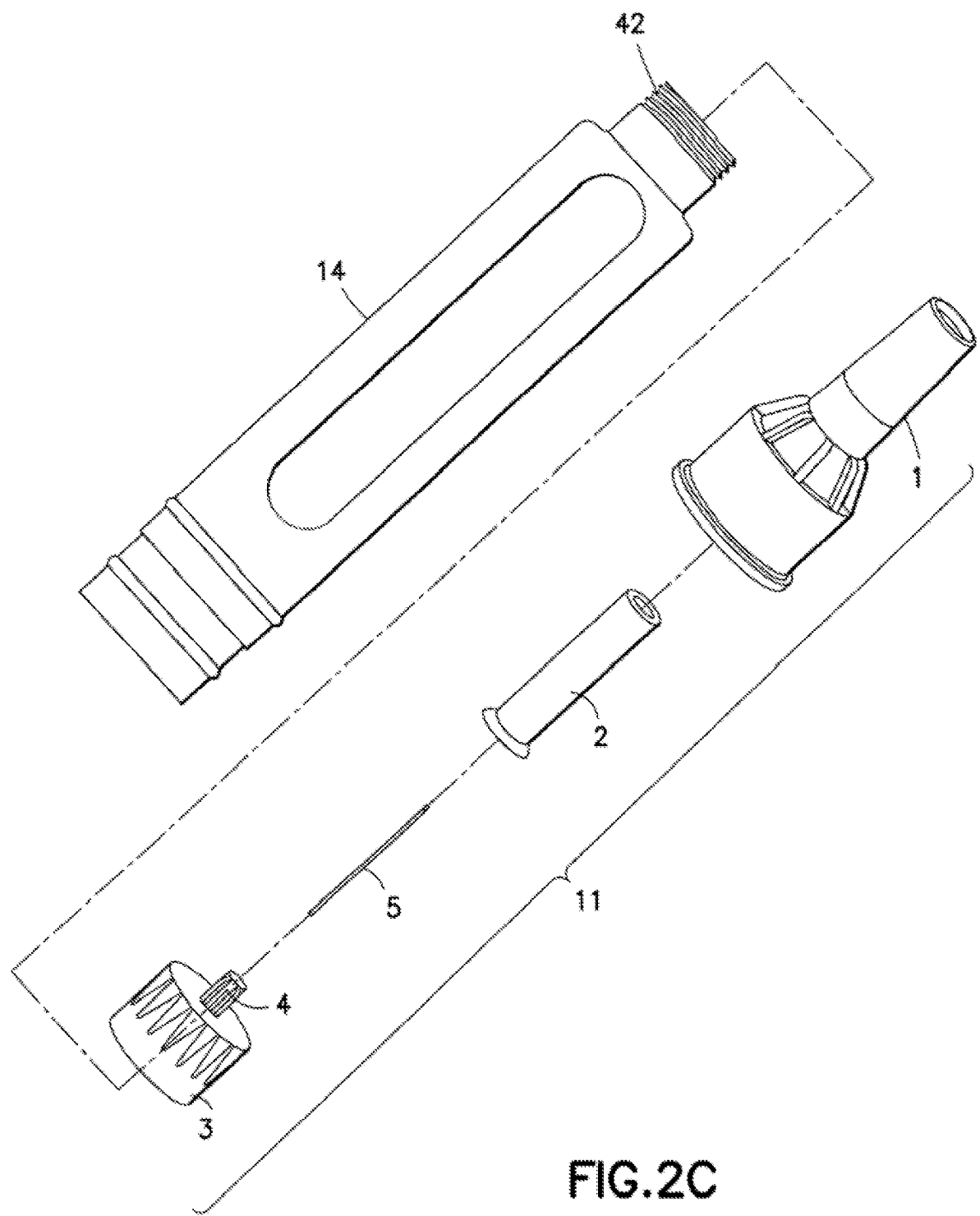
FIG. 2C depicts an unassembled view of a pen needle usable in exemplary embodiments of the present invention.

An exploded perspective view of a pen needle 11 of an exemplary injection pen is shown in FIG. 2C. The pen needle 11 includes the cover (outer shield) 1, an inner shield 2, a needle cannula 5, and a hub 3. During manufacture, a proximal end of the needle cannula 5 is inserted into a center opening in the distal (patient) end 4 of the hub 3 until a predetermined length of the distal (patient) end of the needle cannula 5 remains extended. The needle cannula 5 is secured by epoxy or adhesive in the distal end 4 of the hub 3. To protect users from injury and the needle cannula 5 from being damaged, the inner shield 2 covers the exposed portion of the needle cannula 5. The open proximal end of the inner shield 2 is placed over the exposed portion of the needle cannula 5. The open proximal end of the cover 1 envelops the inner shield 2, needle cannula 5, and hub 3. The distal end of the cover 1 is closed to prevent contamination and damage to the inner components of the pen needle 11, and to prevent injury to anyone who may handle it prior to use. When the user is ready to use the pen needle, the hub 3 is screwed onto threads 42 of cartridge holder 14 of the injection pen it) (FIGS. 1, 2A and 2B), and the cover 1 and shield 2 are separately removed from the hub 3/cannula 5 subassembly by a pulling action. The distal end of the inner shield 2 is closed to protect the user from an accidental needle stick by the needle cannula 5 after the cover 1 is removed. The inner shield 2 is then removed to access the needle cannula 5.

Figure 3A:
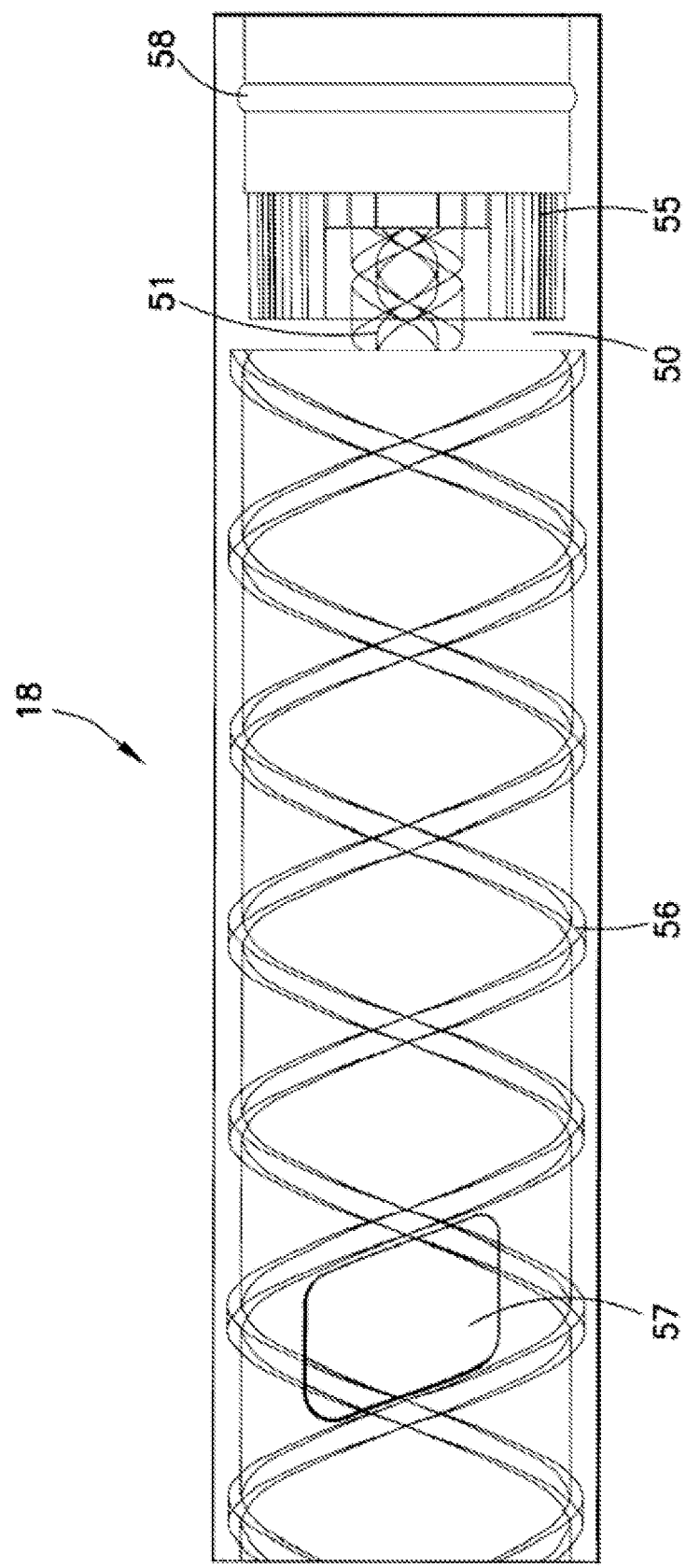
FIGS. 3A and 3B depict views of a body provided in a medication injection pen according to the first exemplary embodiment of the present invention.
Figure 3B:
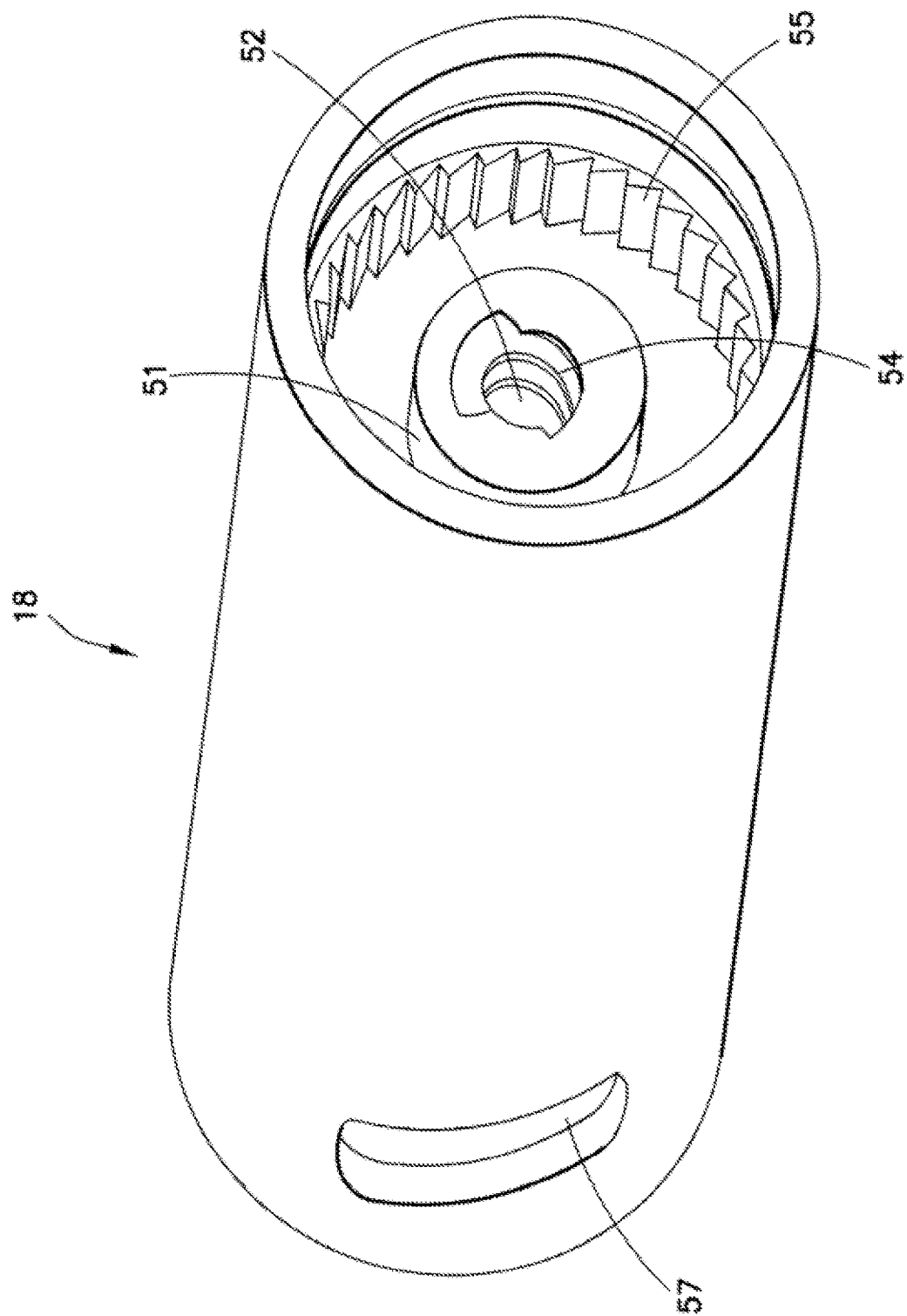

With reference to FIGS. 3A and 3B, the body 18 is generally cylindrical, and includes a cylindrical partition or wall 50 extending across the interior of the body 18 through which a channel 51 is formed comprising an aperture 52. Cylindrical wall 50 effectively divides body 18 into two compartments, a first compartment proximal to wall 50 for housing the plurality of dose setting and injecting components, as shown in FIGS. 2A and 2B, and a second compartment distal of wall 50 for housing the leadscrew brake 32 and connecting to the cartridge holder 14. The channel 51 comprises internal threads 54 threadedly engaging corresponding threads of the leadscrew 26. In an exemplary embodiment, the leadscrew 26 is provided with a non-circular cross-section, in which case, the aperture 52 is defined to allow rotational and thereby axial movement of the leadscrew 26 therethrough. A plurality of second threads 56 are provided on the interior of the body 18 in the first compartment and threadedly engaged with corresponding threads 62 provided on the dose set knob 20, as discussed further below. Body 18 preferably includes a window 57 enabling the user to view a set dose indicated on the outer surface of the dose set knob 20. As described further below, a series of angled steps or teeth 55 are provided on the interior of the second compartment of body 18, circumferentially surrounding the distal end of channel 51. Teeth 55 are provided as part of a unidirectional coupling with the leadscrew brake 32 to allow the leadscrew 26 to rotate through the channel 51 in only one direction, that which causes the leadscrew to expel medication from cartridge 36. In an exemplary embodiment, body 18 also includes a circumferential rib or groove 58 onto which the cartridge holder 14 may be mounted with a snap fit.

Figure 4A:
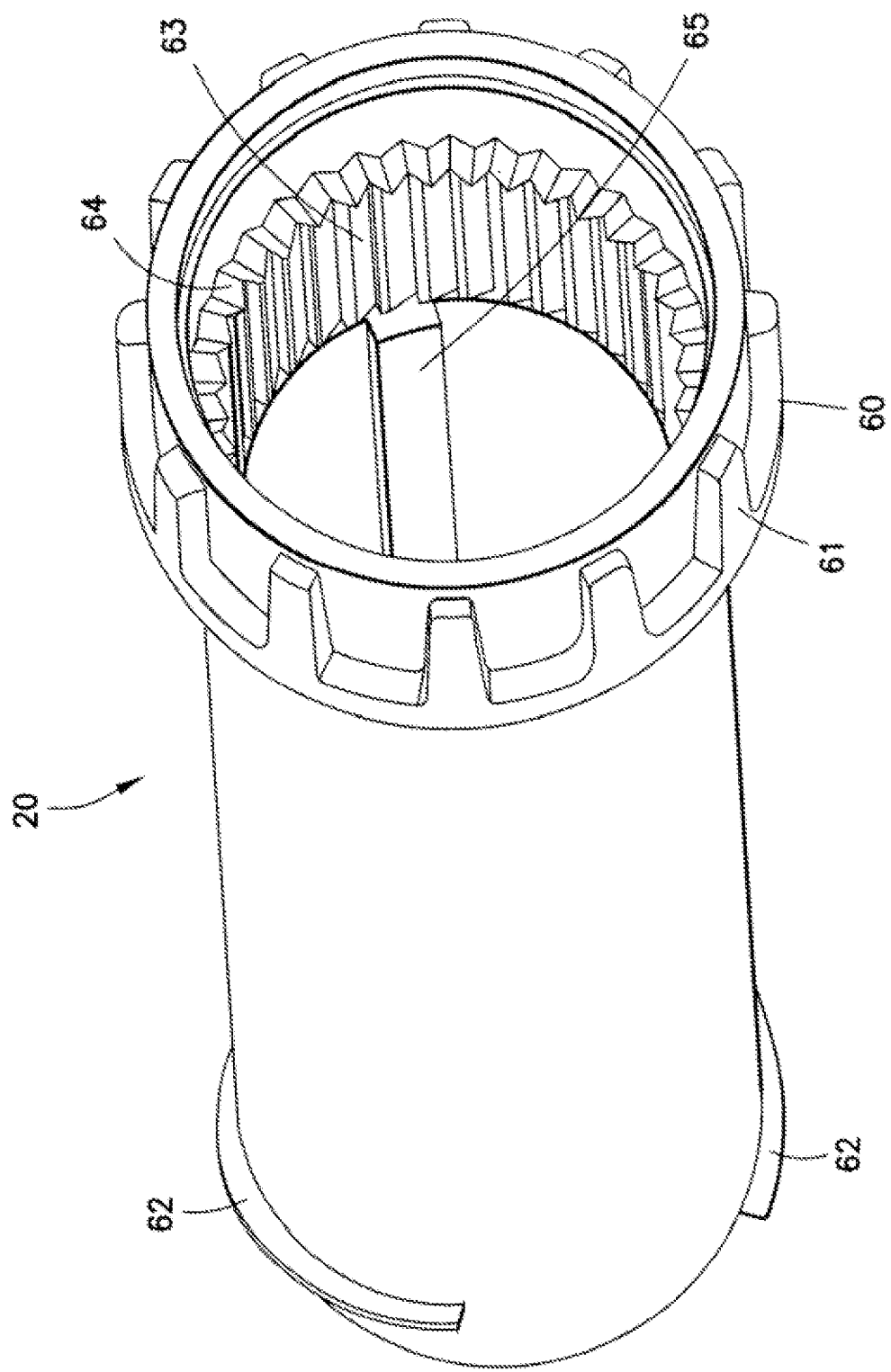
FIGS. 4A and 4B depict views of a dose set knob provided in a medication injection pen according to the first exemplary embodiment of the present invention.
Figure 4B:
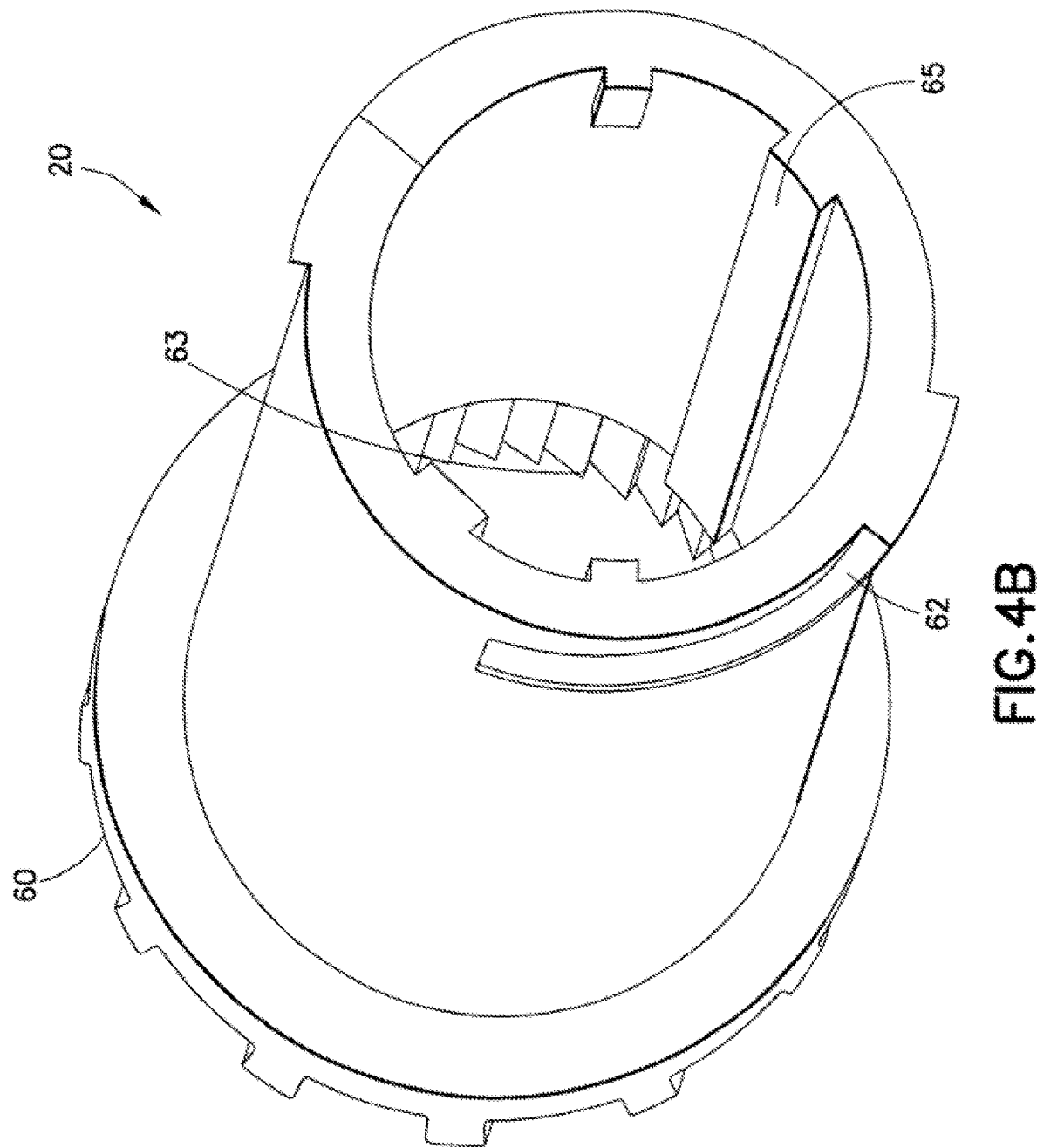

With reference to FIGS. 4A and 4B, a generally cylindrical dose set knob 20 with open proximal and distal ends is provided with an enlarged proximal portion or handle 60 defining a knob-like feature. Handle 60 may include a plurality of grooves 61 enabling a user to securely grip handle 60 to set a dose of medication for an injection. Dose set knob 20 includes at least one thread element 62 provided on its external surface, preferably near the distal end and threadedly engaging corresponding threads 56 on the interior of body 18. An injection dose is set by the user by rotating dose set knob 20 in a predetermined direction. Due to the threaded engagement with the body 18, rotation of the dose set knob 20 translates into axial movement of the dose set knob in the proximal direction extending away from and out of the body 18. Provided on the outer surface of body 18, are a plurality of dosing indicia (not shown) indicating a set dose to be viewed through window 57 provided on body 18.

A plurality of radially directed ridges 63 are provided circumferentially along the interior surface of dose set knob 20 adjacent to handle 60. Ridges 63 provide part of a clicking means in conjunction with an externally directed ratchet element 82 provided on click arms 81 (FIG. 6A, 6B) of click element 30. Ridges 63 each comprise a sloped edge and a flat face for allowing relative rotational movement between the dose set knob 20 and click element 30 in only one direction in which the click arm 81 is enabled to slide over ridges 63, thus providing an audible and tactile signal. Additionally, the proximal edges of ridges 63 define a proximally facing surface having a plurality of teeth 64 disposed thereon. In an exemplary embodiment, teeth 64 are included as part of a clutch mechanism when engaged with corresponding teeth 74 (FIGS. 5A and 5B) disposed on setback member 22. When pressed together during injection, teeth 64 and 74 lock together, thus preventing relative rotation between setback member 22 and dose set knob 20, as further described below. Additionally, during dose setting, teeth 64 provided on the dose set knob 20 function as a shelf, causing axial movement of the setback member 74 together with the dose set knob 20, as the dose set knob is rotated and moved axially out of the body 18. Dose set knob 20 also includes a plurality of longitudinally extending keys or splines 65 provided substantially along the interior surface preferably extending from the open distal end to the enlarged proximal portion 60. Longitudinal splines 65 engage with corresponding grooves 95 provided on the exterior of dose stop member 28 to prevent relative rotation between the dose set knob 20 and the dose stop member 28, but to allow relative axial movement therebetween.

Figure 5A:
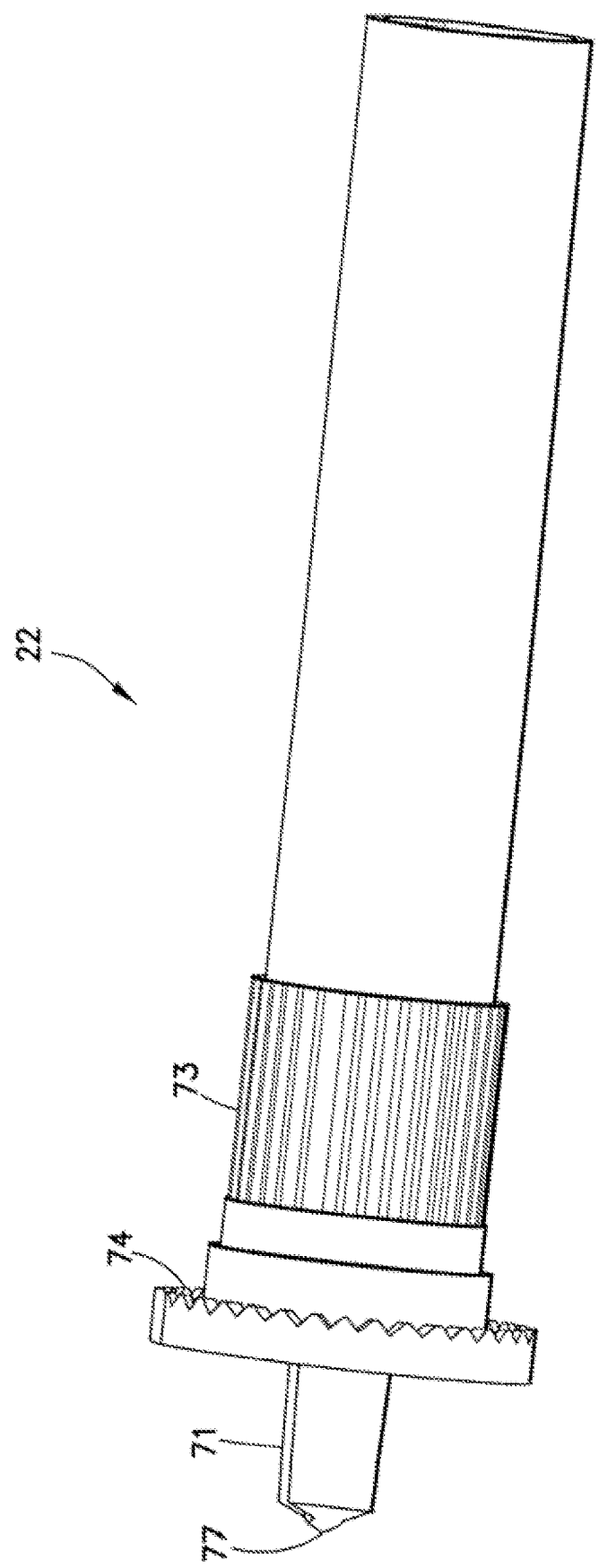
FIGS. 5A and 5B depict views of a setback member provided in a medication injection pen according to the first exemplary embodiment of the present invention.
Figure 5B:
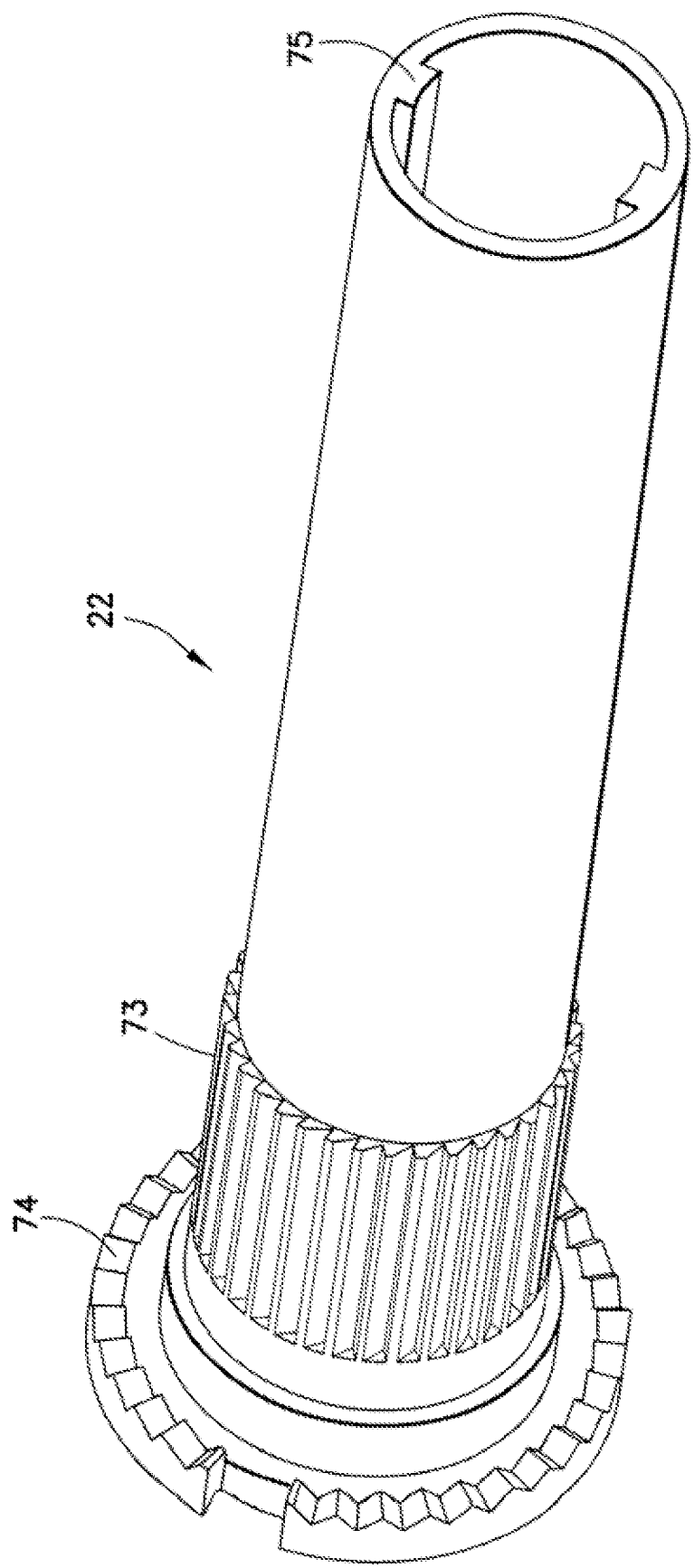

Setback member 22 comprises a generally cylindrical elongated member as shown in FIGS. 5A and 5B, Provided near the proximal end of setback member 22 are a plurality of ridges 73 spaced along the external surface thereof. When the exemplary injection pen 10 is assembled, ridges 73 of setback member 22 face ridges 63 provided on the internal surface of dose set knob 20. Ridges 73 include sloped edges and flat faces for engaging an internally directed ratchet element 84 provided on flexible arm 83 of click element 30. As similarly described above, ridges 73 enable relative rotational movement between the setback member 22 and click element 30 in only one direction in which the internally directed ratchet element 84 is enabled to slide over ridges 73 providing an audible and tactile signal. The allowed direction of relative rotation between the setback member 22 and click element 30 is in the direction opposite that enabled by similar engagement between the dose set knob 20 and the click element 30, so that the relative rotation between dose set knob 20 and setback member 22 is bi-directional.

Figure 6A:
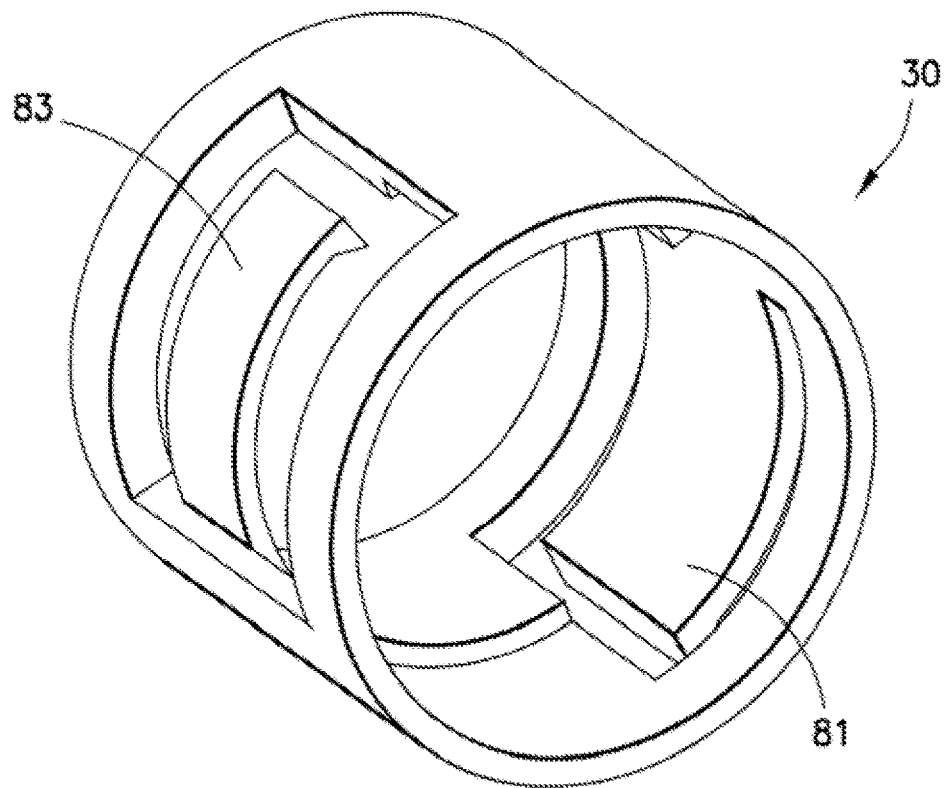
FIGS. 6A and 6B depict views of a click element provided in a medication injection pen according to the first exemplary embodiment of the present invention.
Figure 6B:
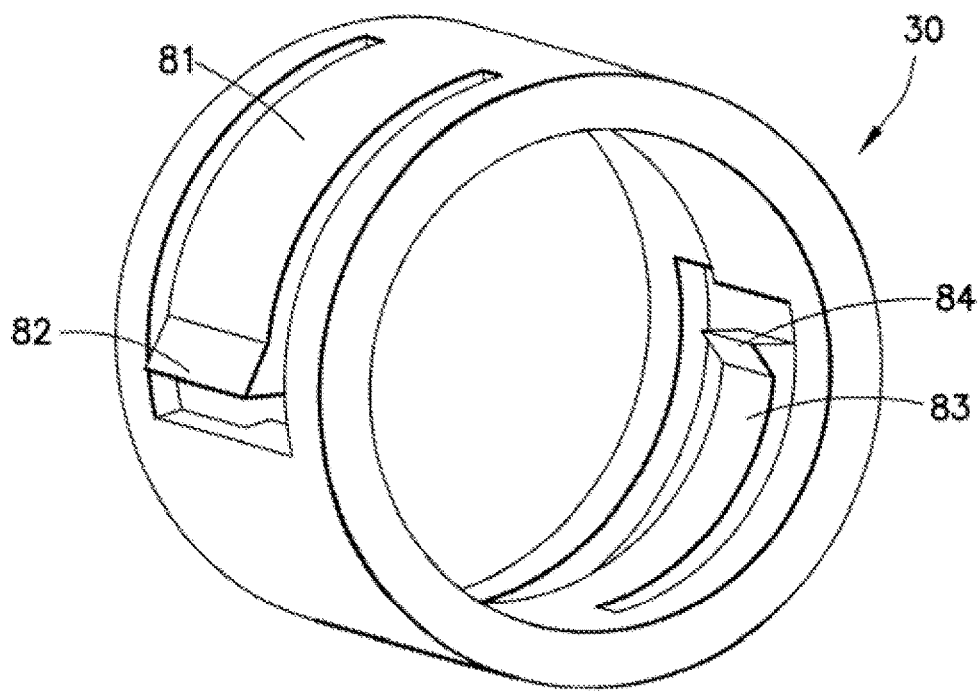

Click element 30 is described with reference to FIGS. 6A and 6B. As shown, click element 30 is a cylindrical tube like element comprising a plurality of radially flexible arms 81 and 83 oppositely disposed from each other. The click element 30 is preferably constructed with a longitudinal dimension similar to the length of the ridge portions 63, 73 provided on the dose set knob 20 and setback member 22, respectively. Flexible arm 81 includes an externally directed ratchet element 82 provided at the free end thereof facing ridges 63 provided on the interior of dose set knob 20. Flexible arm 83, on the other hand, includes an internally directed ratchet element 84 provided at the free end thereof facing ridges 73 provided on the exterior of setback member 22. During dose setting, click element 30 is permitted to rotate relative to both the setback member 22 and dose set knob 20, but in only one direction with respect to each. In other words, during dose setting, click element 30 is rotationally locked to one of the setback member 22 or the dose set knob 20 via flexible arms 83 and 81, respectively, depending on the direction of relative rotation for either normal setting of a dose or dialing back of the set dose. When the dose set knob 20 is rotated in the direction in which ridges 63 are enabled to slide over the externally directed ratchet element 82 and produce an audible signal, the click element 30 does not move rotationally relative to the setback member 22 since such a movement is prevented by an engagement between click arm 83 and ridges 73. Conversely, when the dose set knob 20 is rotated in the opposite direction, the externally directed ratchet element 82 engages with one of the ridges 63 causing the click element to rotate together with the dose set knob 20. In this case, the internally directed ratchet element 84 is now permitted to slide past ridges 73 on the setback member, thereby producing an audible signal.

The exemplary construction of click element 30 described above allows relative rotation in both directions between the setback member 22 and the dose set knob 20. Such a click element is not restricted to the design depicted in FIGS. 6A and 6B. Any similar element(s) enabling bi-rotational movement between setback member 22 and dose set knob 20, as described above, may be implemented in this embodiment, as would be evident to one of ordinary skill in the art.

As shown in FIG. 5A, setback member 22 includes an adapter element 71 for snap-fitting with an internal cavity of push button 34. Push button 34 is of any conventional design, but it is preferred that the snap engagement enables the push button to freely rotate on the adapter element 71. Alternatively, push button 34 may be unitarily formed with the adapter element 71. Additionally, as shown in FIG. 5B, a plurality of longitudinally extending keys or splines 75 are provided along the internal cylindrical surface of setback member 22. Splines 75 are formed to engage corresponding longitudinal grooves 85 provided on the external surface of driver member 24, shown in FIG. 7, thus preventing relative rotation between the setback member 22 and driver 24, while allowing relative axial movement therebetween. With reference to FIG. 7, the driver 24 includes open proximal and distal ends which provide a passage 86 for leadscrew 26. In an exemplary embodiment, passage 86 comprises a non-circular cross-section corresponding to the non-circular cross-section of leadscrew 26, thus preventing relative rotation therebetween. Driver 24 includes a disk 87 formed at the proximal end for snap-engaging with at least one flexible tab 97 provided on the interior surface of dose stop element 28 (FIG. 8A). With the snap engagement, the driver 24 is fixed axially relative to the dose stop element 28, yet is able to rotate relative thereto. Driver 24 may also include one or more flexible legs 88 inwardly biased to engage leadscrew 26. Flexible leg 88 may be provided to reduce any play between the mating cross sections of leadscrew 26 and aperture 86 to improve dose accuracy of the exemplary injection pen 10.

With reference to FIGS. 8A and 8B, a generally cylindrical dose stop element 28 is provided for enabling last dose control so that a dose cannot be set or dialed up that is greater than the amount of medication remaining in the cartridge 36, as further discussed below. Dose stop element 28 includes a plurality of longitudinal grooves 95 on the external surface thereof. Grooves 95 engage with corresponding splines 65 provided on the interior of dose set knob 20, thereby preventing relative rotation therebetween, but allowing relative axial movement. Dose stop element 28 has an open proximal end 91 and open distal end 92, the distal end 92 preferably comprising a section of reduced diameter. Open distal end 92 defines a threaded opening with threads 93 disposed thereon for threadedly engaging corresponding threads 25 of the leadscrew 26 when assembled. Proximal end 91 defines a cavity housing setback member 22, driver 24, and leadscrew 26. Flexible tabs 97 are provided adjacent to the open distal end 92, extending into the interior of the dose stop element 28. A recess 96 or cutout is provided in the external cylindrical wall of the dose stop element defining an area into which flexible tabs 97 are allowed to flex. During assembly, driver 24 is inserted into the open proximal end 91, upon which disk 87 disposed near the distal end of driver 24 engages flexible tabs 97, and causes them to flex outwardly into recess 96 until the disk 87 moves past the flexible tabs, at which time the flexible tabs 97 return to their initial positions to provide a blocking surface for the driver 24, preventing relative axial movement therebetween.

While the above components are described as comprising specific features for engaging and interconnecting other components of an exemplary injection pen, the above components are not limited to these specific features. For instance, instead of the described mating non-circular cross-sections to prevent relative rotation between leadscrew 26 and driver 24, one of ordinary skill in the art will appreciate that similar functionality may be provided using a spline/groove engagement for preventing relative rotation therebetween while also allowing relative axial movement. Conversely, the above described spline/groove features may be replaced with non-circular mating arrangements or other known features for preventing relative rotation while allowing relative axial movement therebetween.

Figure 9A:
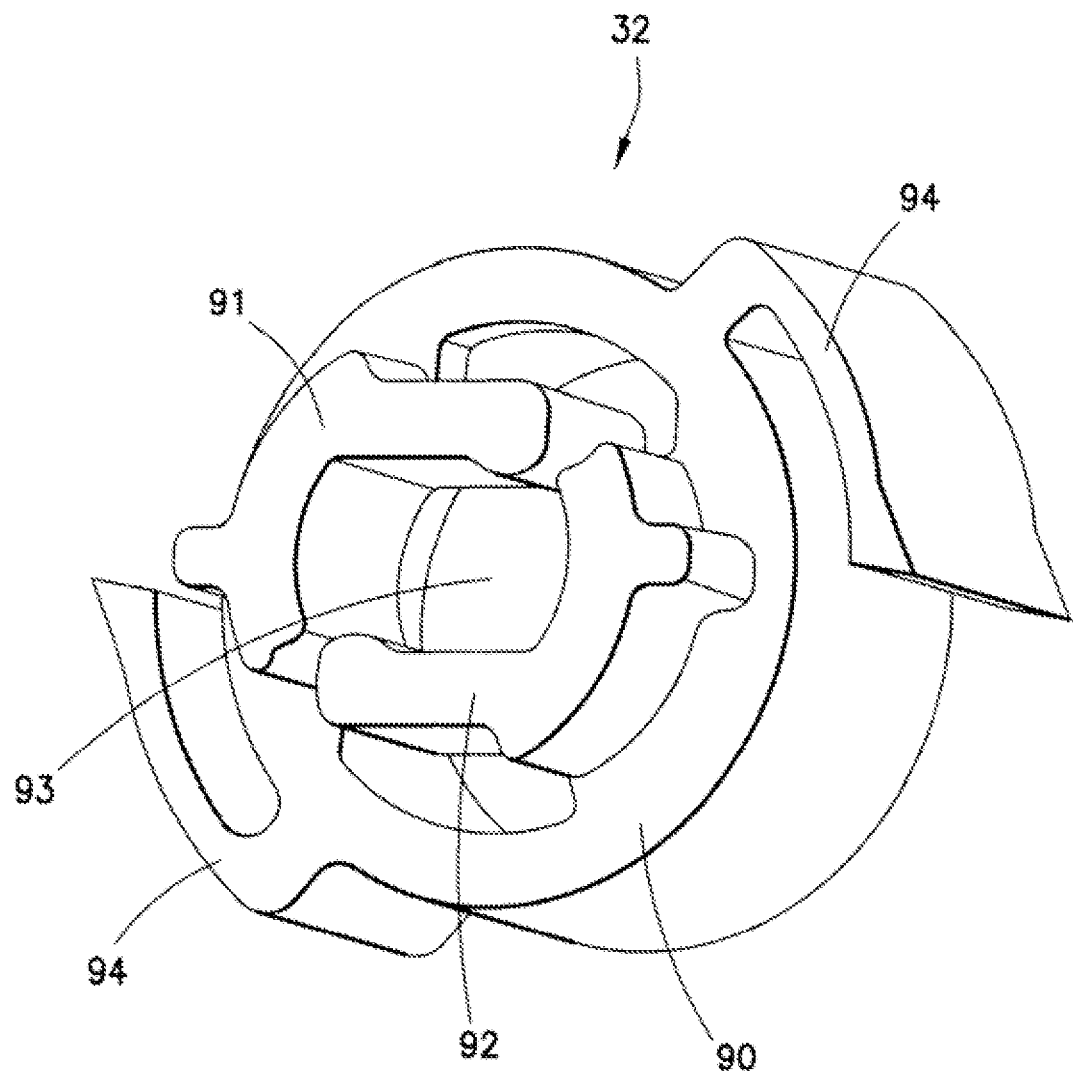
FIGS. 9A and 9B depict views of a leadscrew brake provided in a medication injection pen according to the first exemplary embodiment of the present invention.
Figure 9B:
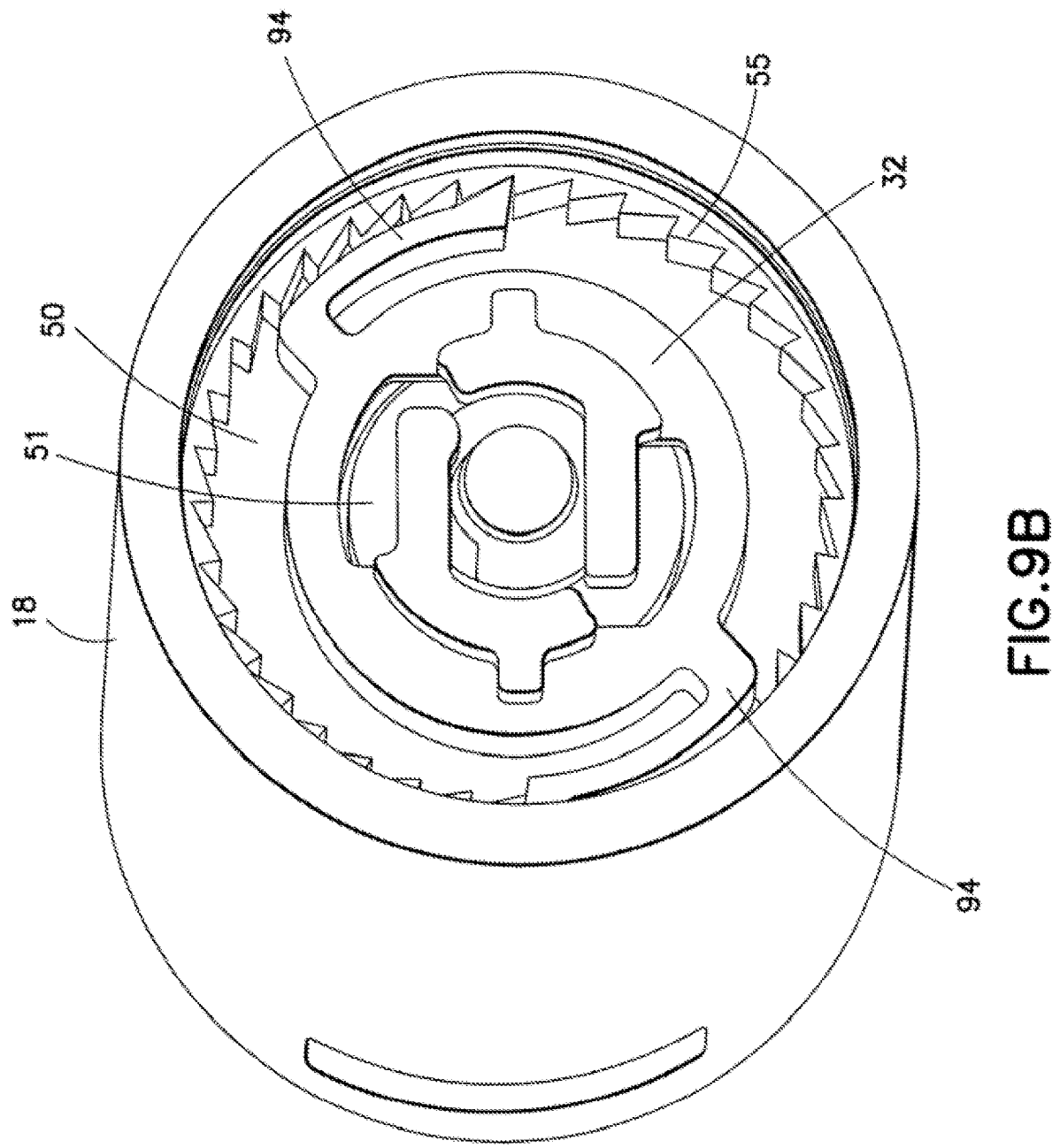

With reference to FIGS. 9A and 9B, leadscrew brake 32 comprises a generally cylindrical housing portion 90 provided with a first diameter large enough to surround channel 51, as shown in FIG. 9B. Extending in the distal direction, a pair of wall portions 92 is provided defining an aperture 93 with a non-circular cross-section to mate with the non-circular cross section of leadscrew 26. Due to the mating non-circular aperture 93, the leadscrew 26 is prevented from rotating with respect to the leadscrew brake. Further, the leadscrew brake 32 comprises a pair of flexible ratchet arms 94 configured to engage the cylindrical ring of ratchet teeth 55 provided on the interior of the body 18 to define a unidirectional coupling therebetween. Ratchet arms 94 are configured to allow rotation of the leadscrew brake 32, and therefore the leadscrew 26, in only one direction with respect to the body 18. The allowed direction is that which causes the leadscrew 26 to rotate through the threaded channel 51 in the distal direction to expel medication. During injection, the leadscrew brake 32 rotates relative to body 18, and ratchet arms 94 ride over the slanted or ramped portion of teeth 55 to produce an audible clicking signal indicating the injection is being performed. Rotation of the leadscrew brake in the opposite direction causes the free ends of ratchet arms 94 to engage the flat faces of teeth 55, which resist ratcheting of the ratchet arms 94 and thereby prevent relative rotation in this direction. Due to the unidirectional coupling between leadscrew brake 32 and teeth 55, an undesired rearward movement of the leadscrew 26 is prevented.

Having described exemplary structures, features and interrelationships between particular elements of the exemplary embodiment of medication injection pen 10 herein, the intended functionality of such an exemplary medical pen device will now be described.

Following assembly of the exemplary elements as shown in FIGS. 2A, 2B, and as described above, to set a desired dose, the patient or user first grips and rotates the enlarged proximal end 60 of the dose set knob 20. The dose set knob 20 is rotated a number of rotations relative to the body 18 until a desired dose is shown through the window 57 on the body 18, Due to the threaded engagement of thread 62 on the dose set knob 20 with the internal thread 56 of the body, the dose set knob is caused to screw out of the proximal end of the body, carrying the setback member 22 along with it by substantially the same distance. The dose stop member 28 is also caused to rotate together with the dose set knob 20 due to the spline/groove engagement between spline 65 provided on the interior of the dose set knob 20 and groove 95 provided on the exterior of dose stop 28. Rotation of the dose stop member 28 causes axial movement of the dose stop member with respect to the body 18 in the proximal direction due to the threaded engagement between threads 93 on the dose stop member and threads 25 of the leadscrew 26. The dose stop element 28, however, moves a shorter distance axially than the dose set knob 20 due to a difference in the pitch of the thread 25 of the leadscrew 26 and the inner thread 56 of the body 18.

During normal dose setting for increasing a set dose, the leadscrew 26 is prevented from rotating with respect to the body 18 in the dose setting direction due to the unidirectional coupling between the leadscrew brake 32 and the teeth 55 disposed on the body 18. Setback member 22 and driver 24, which are rotationally fixed to each other due to spline/groove connection 75/85, are therefore also prevented from rotating with respect to body 18 during dose setting, since the driver is rotationally fixed to the leadscrew via the mating of the non-circular cross-section of leadscrew 26 and the non-circular aperture 86 of the driver 24. Due to the snap fit between disk 87 of the driver 24, and flexible tabs 97 provided on the dose stop member 28, as the dose stop member screws out of the body in the proximal direction, the driver 24 moves axially by the same distance, but does not rotate.

The setback member 22 is interconnected to the dose set knob 20 through the bi-directional click element 30. During normal dose setting, the dose set knob 20 rotates relative to the click element 30, and thus an audible signal is provided due to the inner grooves (3 of the dose set knob 20 sliding past the externally directed ratchet element 82 on flexible arm 81. The externally directed ratchet element 82 tends to slide past ridges 63 in the dose setting direction because the internally directed ratchet element 84 of flexible arm 83 is locked with the ridges 73 provided on the setback member 22, which is prevented from rotating in this direction due to its engagement with the driver 24 and leadscrew 26.

If the user initially sets a dose larger than desired, the set dose can be "dialed back" or reduced by simply turning the dose set knob 20 in the opposite direction. Rotation of the dose set knob 20 in this reverse direction, which is the direction of injection, would normally cause rotation of the leadscrew 26 and thus axial movement of the leadscrew into the cartridge 36. During injection, rotation of the leadscrew 26 is effected due to the coupling between teeth 64 on the dose set knob and teeth 74 on the setback member 22, which is indirectly rotationally fixed to the leadscrew 26. During dial back, however, the dose set knob 20 and setback member 22 are not coupled via teeth 64174 and the dose set knob 20 rotates in this reverse direction relative to the setback member 22 through the click element 30. Reverse rotation of the dose set knob 20, during dial back now causes the internal ridges 63 on the dose set knob 20 to engage and lock with the externally directed ratchet element 82, forcing the click element 30 to rotate in this same direction. The internally directed ratchet element 84 is now caused to slide over ridges 63 provided on the setback member 22, thereby producing an audible signal indicating the dose is being reduced. Ratchet element 84 tends to slide over ridges 73 in this direction since there is less friction provided between ratchet element 84 and ridges 73 than there is between the unidirectional coupling between the leadscrew brake 32 and the body 18. In other words, the force required to dial back a set dose is not great enough to overcome the friction between the ratchet arms 94 of leadscrew brake 32 and the teeth 55 of body 18.

Once a desired dose is set, and the user desires to inject the set dose of medication, the medical injection pen 10 is applied to the skin of the patient to insert the needle cannula 5. The pen needle 11 is attached to the threaded portion 42 of the cartridge holder 14 prior to or after setting the desired dosage, as a matter of user preference. Once the pen needle 11 has been attached to the cartridge holder 14 and inserted into the patient, the push button 34 is depressed. The axial force applied to the push button 34 by the user causes the teeth 74 on the setback member 22 to engage with the teeth 64 on the dose set knob 20 to mesh and rotationally lock the setback member 22 with the dose set knob 20, forming an injection coupling. The applied force causes the dose set knob 20 (due to a non self-locking threaded engagement with the body 18 via threads 56 and 62) to rotate in the direction opposite that which occurs during normal dose setting. This rotation is now imparted to the setback member 22 and therefore the driver 24 (due to the spline/groove connection 75, 85). Since the driver 24 mates with the non-circular cross-section of the leadscrew 26, the leadscrew is also caused to rotate relative to body 19, which translates into axial movement of the leadscrew into the cartridge 36 to expel a dose (due to the threaded engagement between threads 25 on the leadscrew and threads 54 disposed on channel 51 of the body 18). Axial movement of the leadscrew in the distal direction urges the spinner 16 against the plunger 40 to expel medication from the cartridge 32. The injection force is greater than the frictional force in the leadscrew brake 32, and hence the leadscrew brake allows rotation of the leadscrew 26 in this direction during injection. As the leadscrew brake 32 rotates with the leadscrew 26, oppositely disposed ratchet arms 94 slide over the teeth 55 disposed on the interior of body 18 to produce a clicking sound as the injection is carried out.

The dose administration process described above may be repeated until the medication in the cartridge 36 is spent. Prior to expelling the last dose from the cartridge 36, it is desired to ensure that the last dose expelled is consistent with the dose set by the user. In other words, the user should not be able to set a dose for an amount greater than the remaining volume of medication in the cartridge 36. This last dose control is realized when threads 93 disposed on the dose stop element 2K abut against a non-threaded portion of the leadscrew 26 at its proximal end, preventing further rotation of the dose stop member 28 on leadscrew 26, When this occurs, the indicia on the dose set knob 20, read through window 57, indicate the last remaining injectable volume of medication in the cartridge 36. Once the dose stop member 28 is prevented from rotating further, the dose set knob 20 is also prevented from further rotating in this direction for setting a larger dose, due to the spline/groove engagement 65/95 between dose set knob 20 and dose stop member 28.

During dose setting, the dose stop member 28 changes its relative position on the leadscrew 26 based on the number of rotations of the dose set knob 20. Axial movement of the dose stop member 28 during dose setting is by substantially the same distance as the leadscrew 26 moves into cartridge 36 during injection. The length of axial movement of leadscrew 26, and therefore the volume of medication to be expelled, is determined in part by the thread pitch of the leadscrew threads 25 and threads 54 of the body, which is substantially the same as the pitch of the threads 93 of the dose stop member 28. Thus, the relative position of the dose stop member 28 on the leadscrew 26 throughout administration is indicative of the remaining dosage amount in the cartridge 36. The dose stop member maintains its relative position on the leadscrew 26 during injection due to its spline/groove engagement 65195 with the dose set knob 20. During injection, the dose sent knob 20, dose stop member 28, setback member 22, driver 24 and leadscrew 26, are all rotationally locked together. Since the threads 93 of the dose stop member 28 and the threads 54 of the body 18 are of substantially the same pitch, simultaneous rotation of the dose stop member 28 and leadscrew 26 results in the same axial movement. Thus, during injection, the dose stop member 28 does not move axially relative to leadscrew 26, and therefore maintains its relative position with respect to the leadscrew as determined during the dose setting procedure. After administration of the last dose, if the injection pen 10 is reusable, the cartridge can be replaced, whereas, if the pen is disposable, the entire pen 10 may be disposed of.

As will be appreciated by those skilled in the art, various modifications can be made to the above exemplary embodiments without substantially altering the functionality of the injection pen 10. For example, such modifications may be made to ease the assembly of the various components, reduce the complexity of manufacturing, reduce the number of elements, or provide some additional improved functionality. Some such exemplary modifications are described below.

In one alternative embodiment, teeth 64 on the dose set knob 20, described above as part of an injection coupling with corresponding teeth 74 (FIGS. 5A and 5B) disposed on setback member 22, can generate dose setting click signals in the absence of click element 30. A spring element or wave washer with similar functionality may be provided to bias the teeth 74 of setback member 22 toward the corresponding teeth 64 provided on the dose set knob 20, so that they are in constant meshed engagement. The spring force, however, is easily overcome by relative rotation between the dose set knob 20 and setback member 22, which causes the corresponding teeth 64/74 to slip over each other producing an audible and tactile signal.

In another exemplary embodiment, an alternate injection coupling is provided between a modified dose set knob 20 (teeth 64 removed) and a modified setback member 22', shown in FIG. 10. In this embodiment, the injection coupling described above with respect to teeth 64 on the dose set knob 20 and corresponding teeth 74 on the setback member 22, is replaced by an extended surface 101 provided near the proximal end of the setback member 22', the extended surface 101 being defined by a larger diameter with respect to ridges 73, Click element 30 includes a first surface 102 positioned co-axially on and surrounding the extended surface 101. During the dose setting operation, click element 30 is positioned on setback member 22', such that click arms 81 and 83 are free to flex and slide past ridges 73 and 63, respectively. In this embodiment, the dose setting and dial back mechanism is unchanged. During injection, however, upon the user applying an injection force to push button 34, the setback member 22' is pushed into the dose set knob 20 and into click element 30. As the setback member 22' moves axially toward click element 30, the extended surface 101 is moved into engagement with click arm 83, as shown in FIG. 10B, In this position, click arm 83 is prevented from flexing radially inward to slide past grooves 63 in the dose set knob, thus locking click element 30 to dose set knob 20. Relative rotation of the dose set knob 20 with respect to the setback member 22' in this direction during dose setting would have enabled the ratchet arm 83 to ride over ridges 63 to reduce a set dose. During injection, however, ratchet arm 83 is now prevented from flexing away from ridges 63, and thus prevented from sliding over ridges 63, by the blocking engagement of extended surface 101. Accordingly, the setback member 22' is now rotationally locked to dose set knob 20 via non-sliding engagement with ratchet arm 83, thus enabling injection of a set dose, as described above.

In another embodiment, the exemplary injection pen 10 is modified to facilitate the manufacture of injection pens providing different dosing needs. For example, an injection pen for administering a first medication may desire finer dosing intervals for more precise dosage control than that of another medication. To utilize the same dose setting and injection functionality of the exemplary injection pen described above, it is desired to be able to provide a plurality of pens meeting the various dosing needs with greater compatibility, so as to reduce the complexity of manufacturing multiple such pens.

Figure 11A:
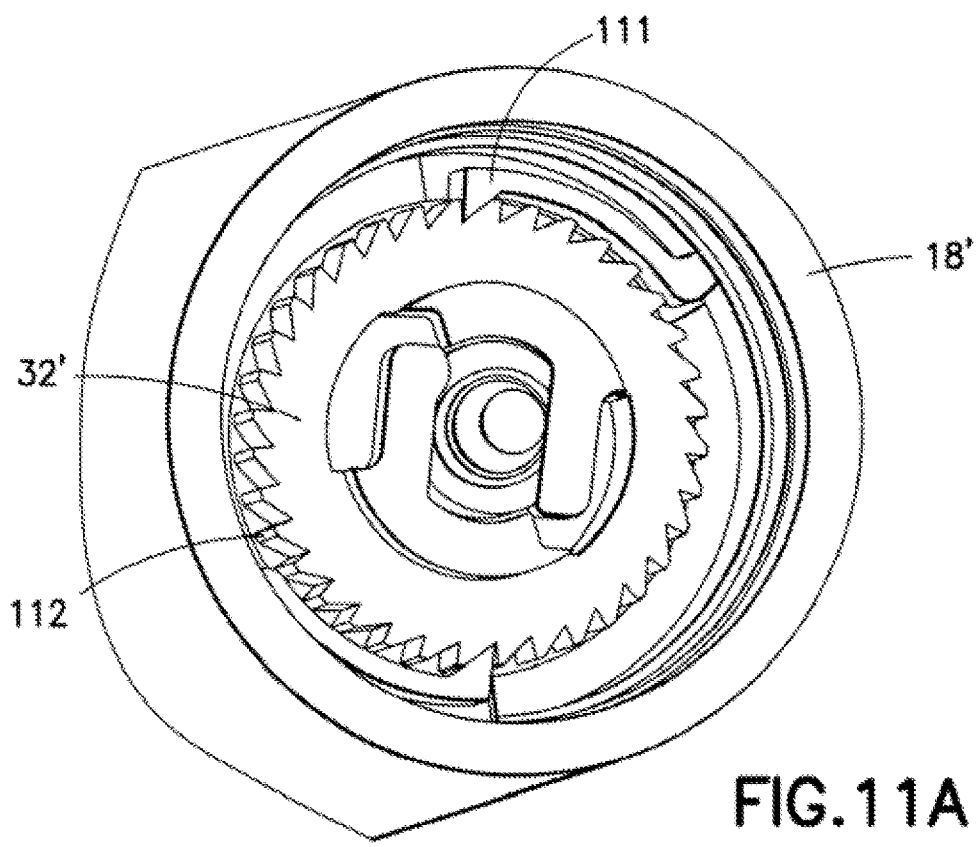
FIGS. 11A-11F depict views of alternative leadscrew brake and threaded insert embodiments provided in a medication injection pen according to the first exemplary embodiment of the present invention.

One such modification is made to the embodiment illustrated in FIG. 9B to switch the ratchet arms 94 provided on the leadscrew brake 32 with the ratchet teeth 55 provided on body 18, as shown in FIG. 11A. As shown, the body 18' now includes ratchet arms 111 and the leadscrew brake 32' now includes teeth 112. Engagement between ratchet arms 111 and teeth 112 serves to provide similar unidirectional functionality as described in the previous embodiment. Leadscrew brake 32' in this alternative embodiment facilitates a change in a desired injection click interval necessitated by a desired change in a dosing interval. For example, the injection clicks realized by relative rotation of the leadscrew brake 32' preferably correspond to a dose increment, and are related to the spacing of the teeth 112. If the dose increment is changed to have a greater or smaller interval, a leadscrew brake with a corresponding spacing of teeth 112 is assembled in the injection pen as shown, as opposed to providing a new body 18 with the desired spacing or teeth 55, as in the earlier embodiment. The smaller leadscrew brake 32 is easier and less costly to manufacture than the body 18, and hence it is advantageous to replace leadscrew brake 32 in the modified injection pen as opposed to replacing the body 18.

Figure 11B:
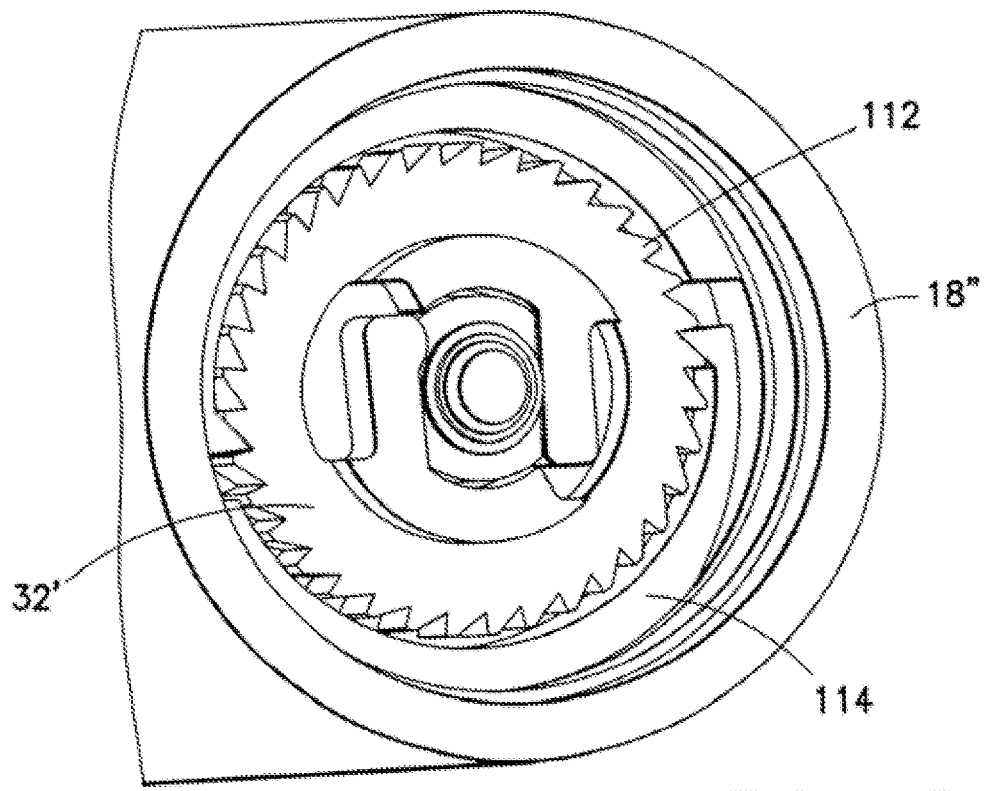

A further modification, shown in FIGS. 11B-11F, enables an easier change of the thread pitch of the leadscrew if desired to increase or decrease a dose rate. For example, the threads 25 of the leadscrew 26 may be modified to include a larger pitch, so that the same number of rotations of the leadscrew results in greater axial movement of the leadscrew into cartridge 36 and therefore a larger dose volume. In the previous embodiment, if the threads 25 of the leadscrew 26 are modified, the threads 54 of the body are also modified accordingly. The additional modification shown in FIG. 11B provides an insert 114 which replaces the features of the partitioning wall 50 and channel 51 with threads 54 disposed thereon of the exemplary embodiment (see FIG. 3A). Insert 114 is a nut-like element with ratchet arms 115 disposed thereon. Insert 114 comprises a wall 118 with an aperture 119 therethrough. Aperture 119 is defined by a cylindrical channel 116 with threads 117 disposed on the interior thereof. Body 18" now includes a shelf or ledge 121 forming a contact surface engaging with a proximal surface of insert 114 to determine axial placement of the insert 114 into body 18". Shelf 121 comprises at least one protrusion member 122 configured to engaged a corresponding recess 120 on the proximal face of insert 114. Engagement between protrusion 122 and recess 120 prohibits relative rotational movement between insert 114 and body 18", Alternatively, any similar key/groove type structure may be provided to limit relative rotational movement between insert 114 and body 18".

Figure 11C:
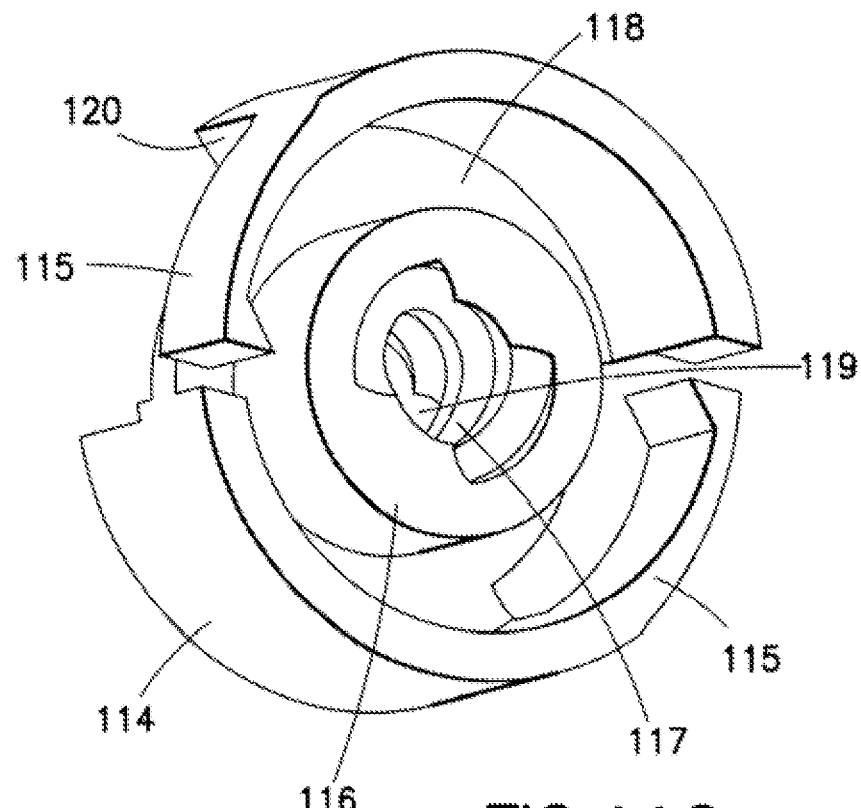
Figure 11D:
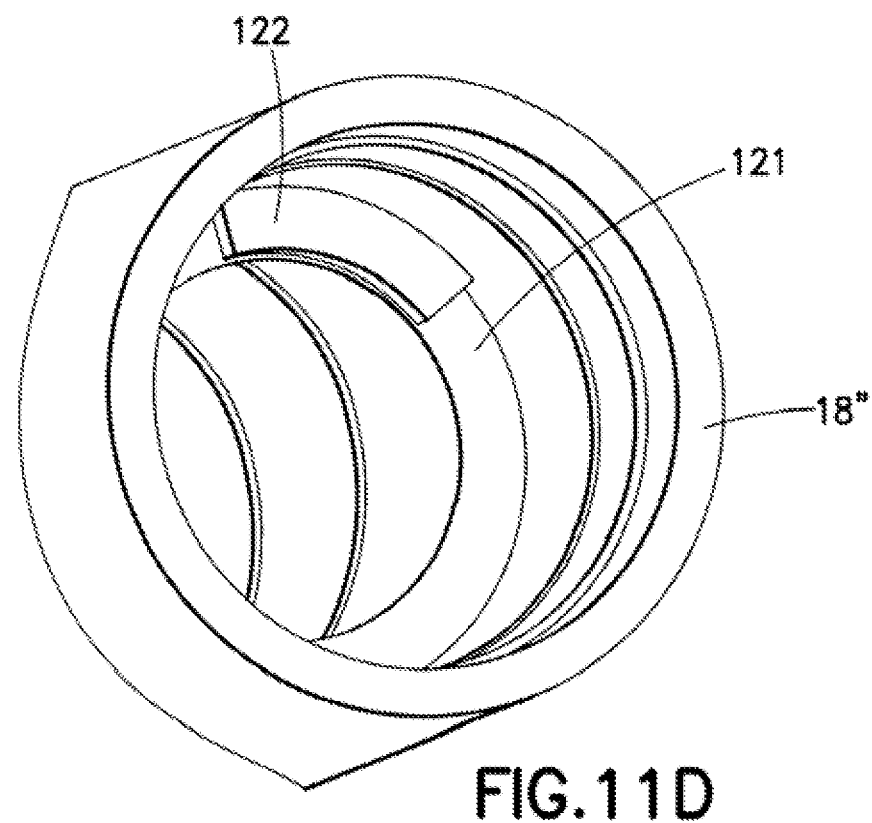
Figure 11E:
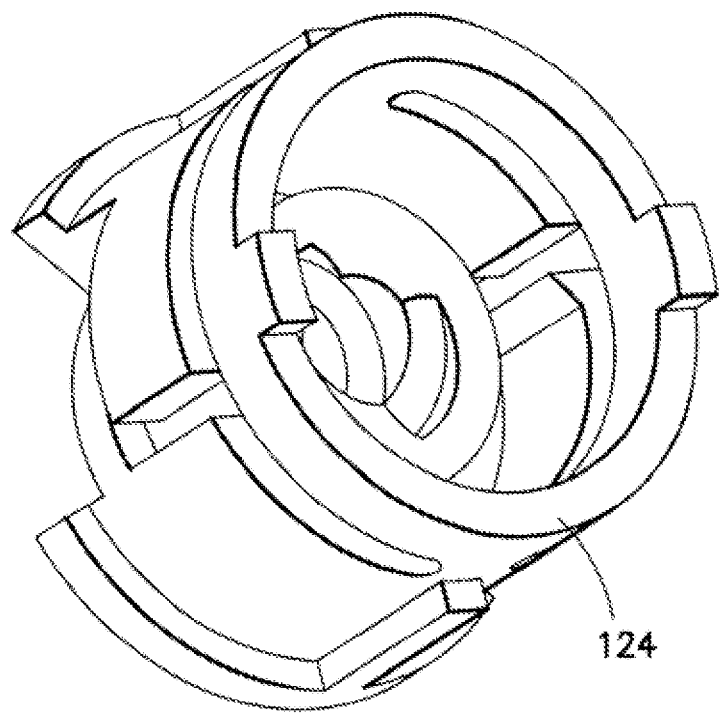
Figure 11F:
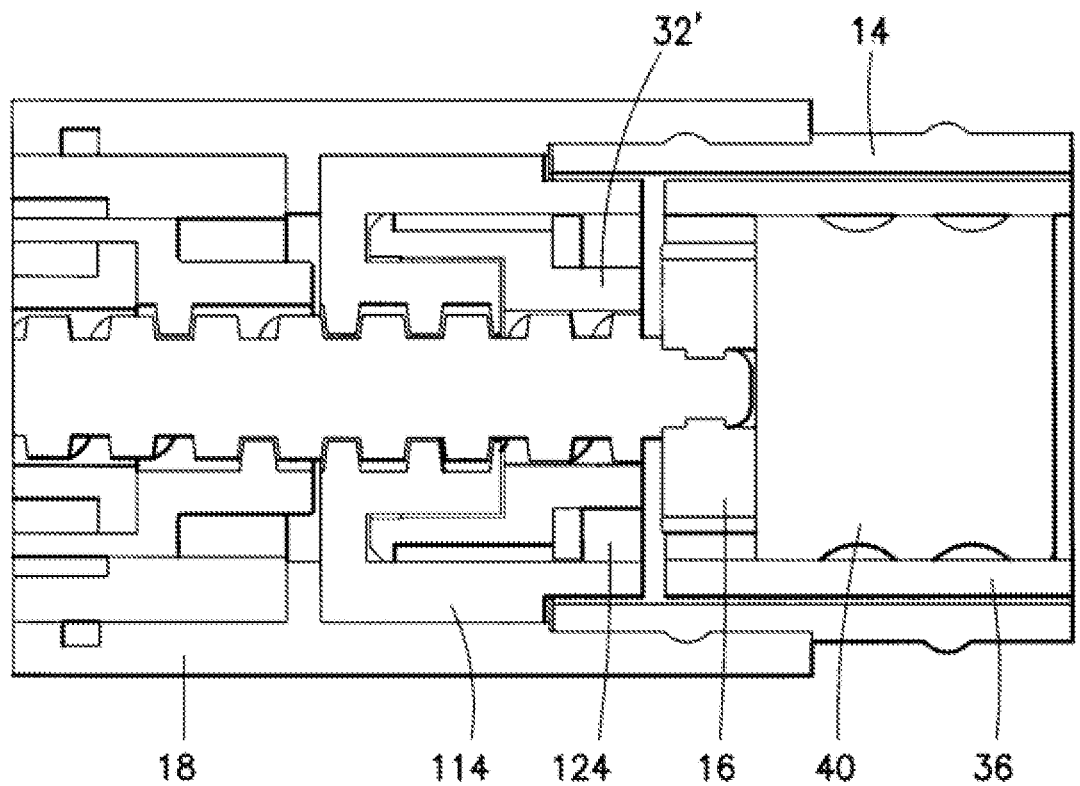

Insert 114 may also be provided with an additional molded spring feature 124 to maintain the positioning of insert 114 against shelf 121 in body 18". Molded spring feature 124 also presses against cartridge 36, as shown in FIG. 11F, to prevent the cartridge from moving when the needle 5 is inserted into the cartridge septum 38 prior to injection. This feature provides greater accuracy in dose injection and prevents undesired wasting of medication. In prior art injection pens, the cartridge may be allowed to move a slight distance in the proximal direction during this operation, resulting a small waste or "drool" of the medication.

Figure 12B:
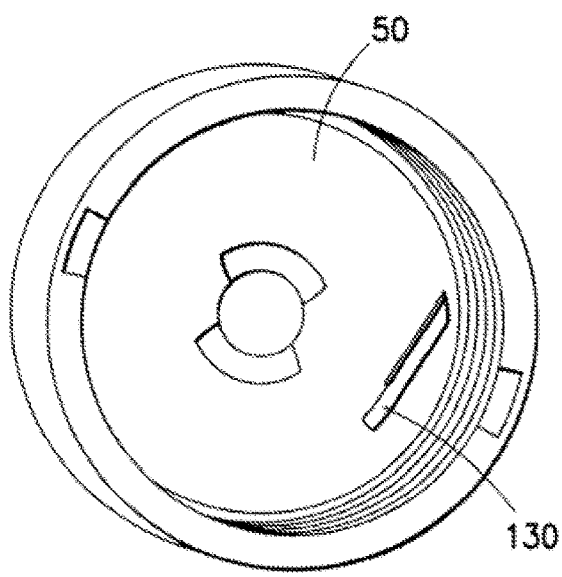
Figure 12C:
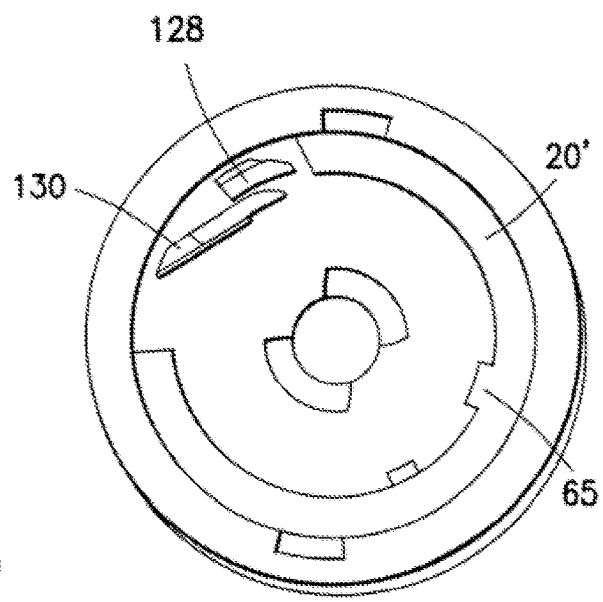
Figure 12D:
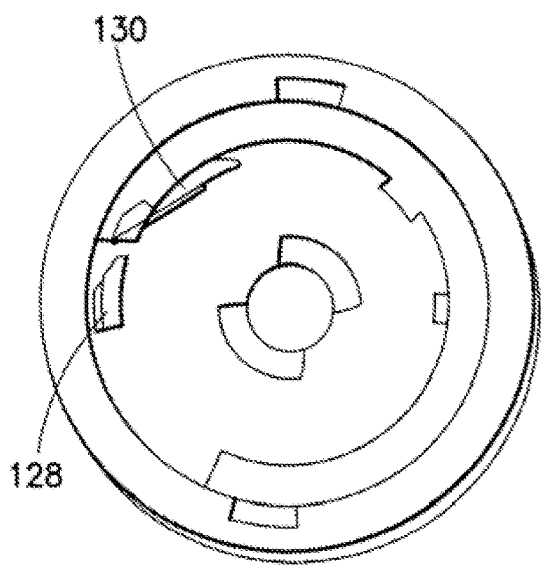

In another exemplary embodiment, an end of injection click or signal is provided by a modified dose set knob 20' including a radially flexible leg 128 near the distal end of dose set knob 20' extending in the distal direction. Flexible leg 128 interacts with an angled protrusion 130, shown in FIG. 12B, disposed on a proximal surface of partitioning wall 50 of the body 18. Angled protrusion 130 is preferably fixed to partitioning wall 50 at only one end, which is the end spaced farther away from the internal surface of body 18. At a zero dose position, when the dose set knob 20' abuts partitioning wall 50, flexible leg 128 is positioned near protrusion 130, but not in touching engagement. Upon setting of a desired dose, as the dose set knob 20' is rotated, flexible leg 128 moves between the angled protrusion 130 and an internal surface of body 18, as shown in FIG. 12C. Since the angled protrusion 130 is not fixed to the partitioning wall 50 at the end closest to the internal surface of the body 18, the angled protrusion flexes radially to allow passage of the flexible leg therebetween and reduce the friction for initially overcoming the protrusion during dose setting. Once flexible leg 128 passes behind protrusion 130, continued rotation of the dose set knob 20' will result in axial movement of the dose set knob away from partitioning wall 50 so that the flexible leg 128 no longer interacts with protrusion 130. Normal setting of the dose is now performed.

Figure 12E:
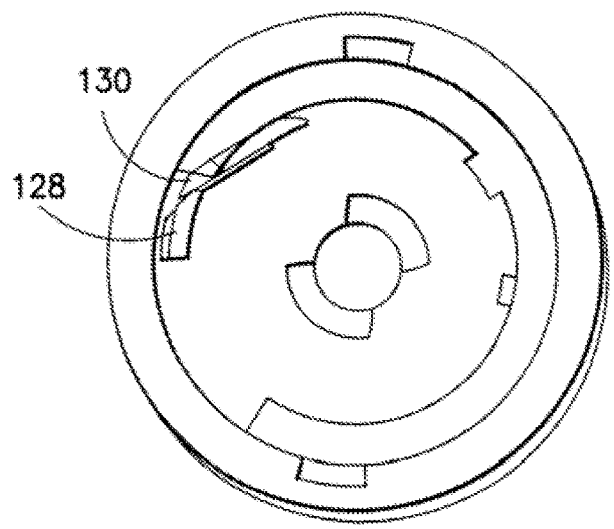

As the set dose is injected, dose set knob 20' screws back into body 18 and moves toward partitioning wall 50. As the injection is nearing its end, flexible leg 128 once again engages protrusion 130 as shown in FIG. 12E. This time, as flexible leg 128 abuts against protrusion 130, it is not allowed to pass between the protrusion 130 and the internal surface of body 18. Now, the flexible leg 128 is caused to flex radially inward to slide past protrusion 130 until it moves past the end of protrusion 130, at which time flexible leg 128 snaps against the internal surface of body 18 providing an audible and tactile signal. At this point, the set dose is completely delivered and the injection pen is at a zero dose position.

Figure 13:
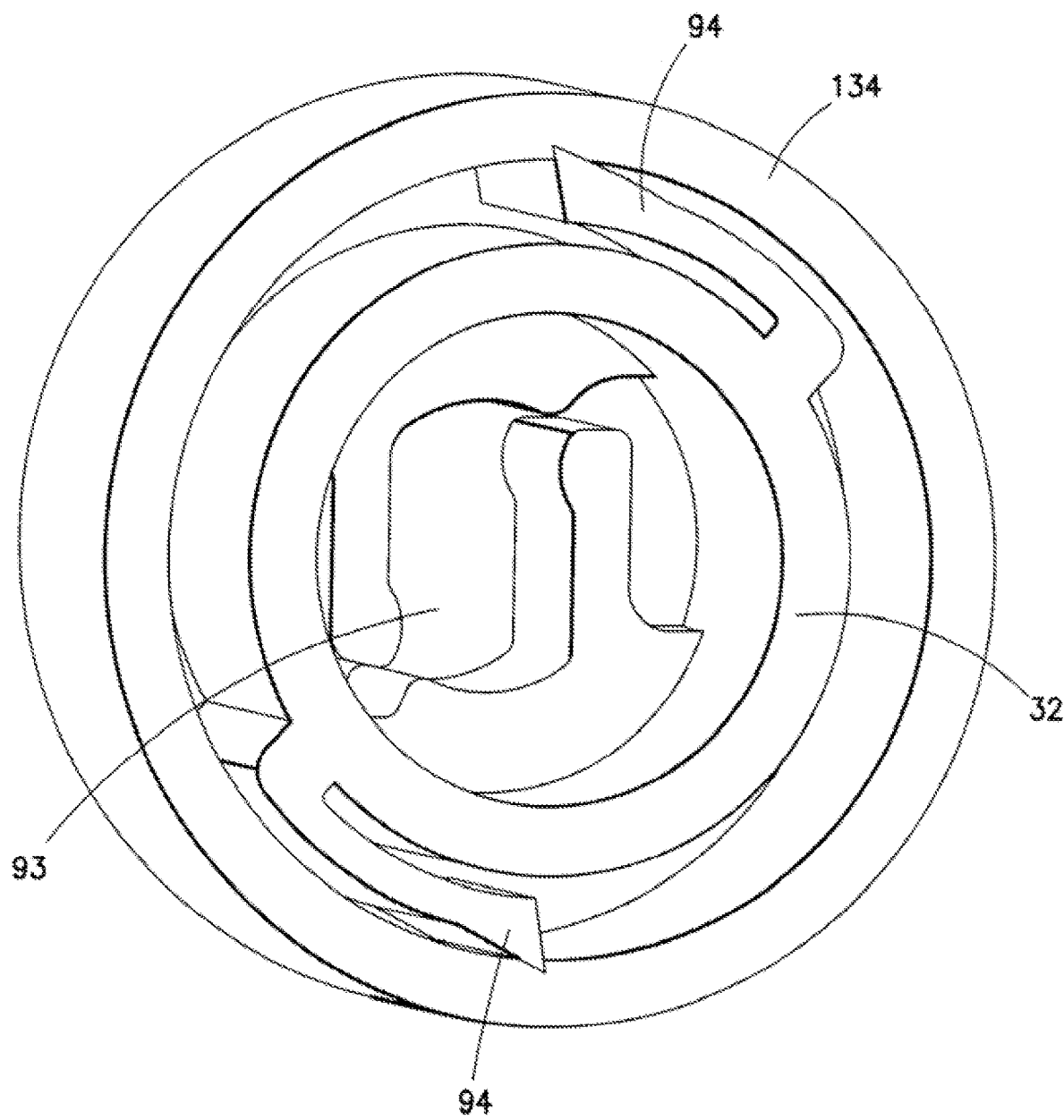
FIG. 13 depicts a view of a muted injection click mechanism in a medication injection pen according to the first exemplary embodiment of the present invention.

In one embodiment, an end of dose click may be provided as a distinct signal distinguishable from the injection clicks provided by the leadscrew brake 32 as discussed above with respect to FIG. 9. In another embodiment, however, the injection clicks are muted, and a user senses only the end of injection click provided between the flexible leg 128 and protrusion 130. One way to mute the injection clicks is to replace ratchet teeth 55 provided on the body 18 with a rubber like ring or brake 134, as shown in FIG. 13. During injection, the leadscrew brake 32 still rotates with respect to body 18, but in this embodiment, ratchet arms 94 slide along the surface of the rubber brake 134 without providing an audible or tactile signal. Rubber brake 134 is fixed to the body 18 using an adhesive or other structure, so that it does not rotate relative to the body 18, and therefore is still capable of functioning as a unidirectional coupling with leadscrew brake 32. Ratchet arms 94 of the leadscrew brake 32 are preferably beveled or otherwise configured to grip the rubber brake 134 to prevent relative rotation therebetween, similar to the embodiment discussed in FIG. 9B. Additionally, one of ordinary skill in the art will appreciate that rubber brake 134 may be modified as similarly discussed in FIGS. 11A and 11B.

Figure 14A:
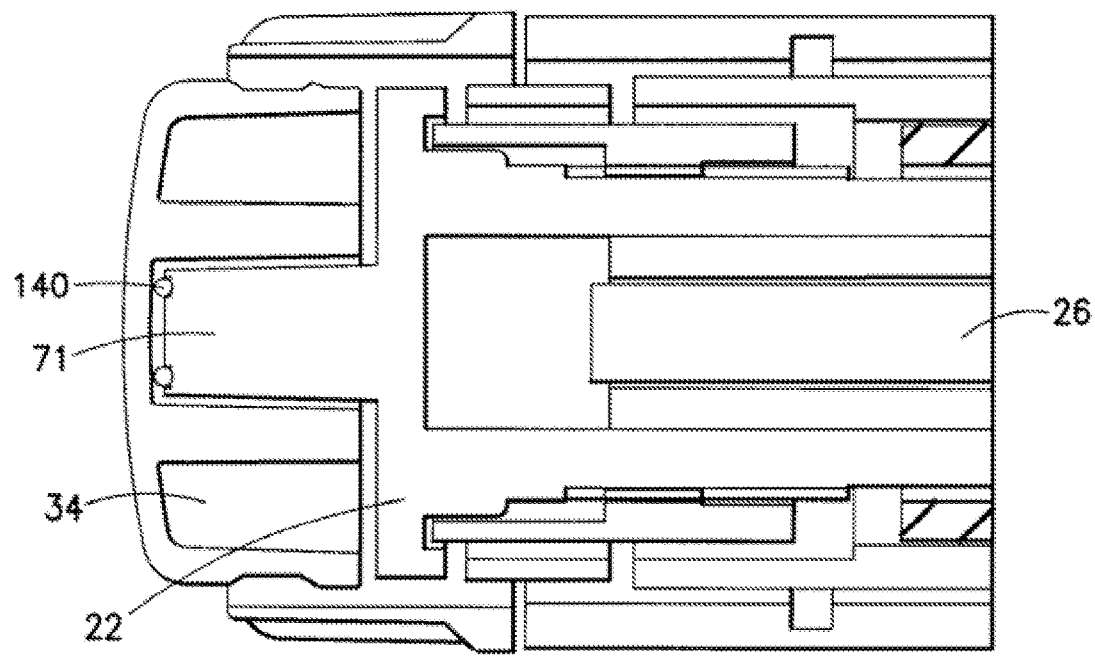
Figure 14B:
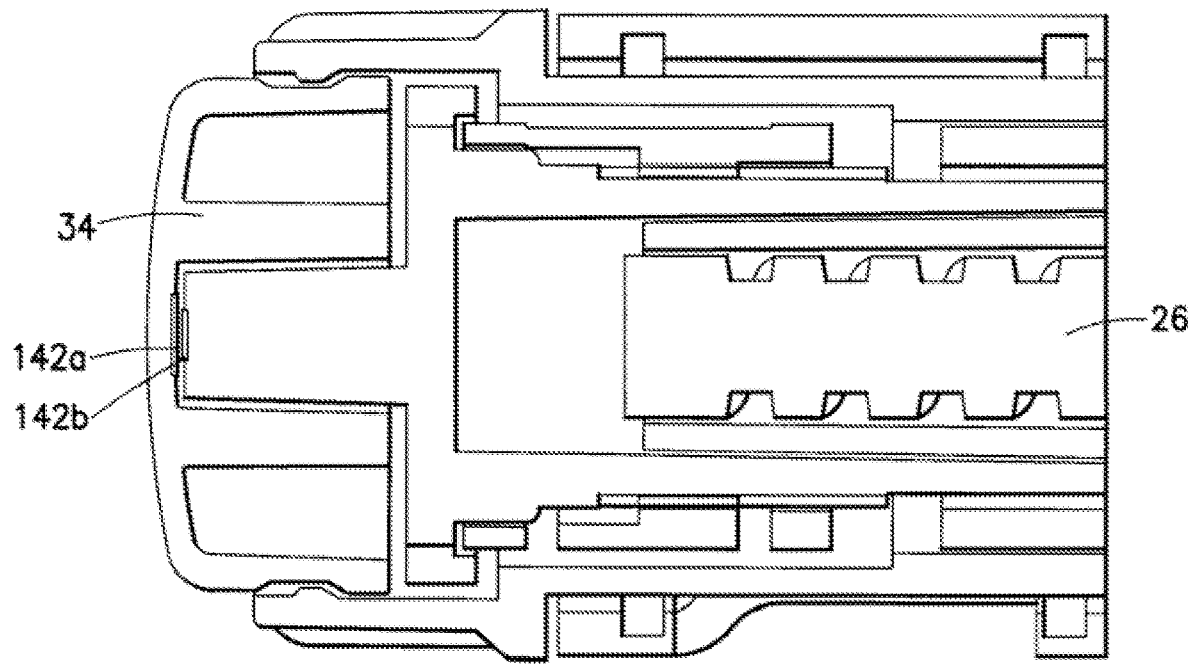

In another exemplary embodiment, an element or elements are added to improve the mechanical efficiency of an exemplary injection pen 10, by eliminating or reducing the friction between elements rotating relative to each other or those moving axially with respect to each other. One particular engagement with undesirable friction is between the push button 34 and the adapter element 71 provided on the setback member. During dose setting and injection, push button 34 preferably rotates freely on adapter element 71. In an exemplary embodiment, as partly shown in FIG. 5A, adapter element 71 includes a point 77 provided at the center of the axis of rotation of the setback element 22. This point 77 contacts push button 34 near its center of rotation. Providing such a contact surface between these elements at or near the center of rotation reduces frictional torque between these elements during relative rotation, and thereby increases efficiency. To further reduce the friction between setback member 22 and push button 34, one embodiment includes at least one rolling ball (i.e. ball bearing) 140 situated between an internal surface of the push button 34 and a surface of the adapter element 71, as shown in FIG. 14A. Rolling balls 140 function to translate sliding friction between engaging elements into a reduced rolling friction. In another embodiment, shown in FIG. 14B, a pair of magnets 142a and 142b with the same polarity are provided on adjacent contact surfaces facing each other. For instance, a first magnet 142a is provided on the interior of push button 34, whereas the second magnet 142b is provided on a contact surface of adapter element 71 facing the first magnet. Due to the same polarity between magnets 142a and 142b, the resulting repulsion force reduces the contact force between these two surfaces, thus reducing friction therebetween without affecting the push force required for injecting medication. One of ordinary skill in the art will appreciate that the above methods may also be implemented in combination. Further, such methods may be implemented between any two components with a linear or rotational contact surface, to further improve mechanical efficiency.

Figure 15A:
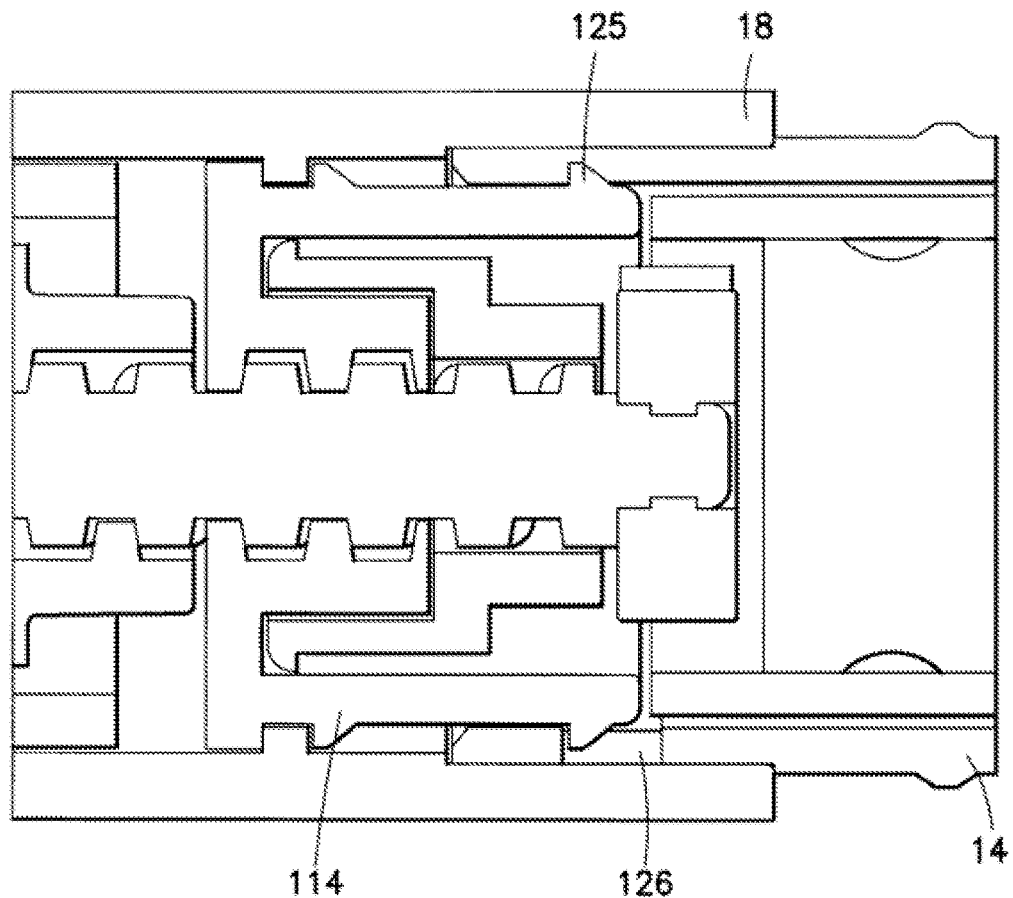
FIGS. 15A and 15B depict exemplary mechanisms for connecting a cartridge to a medication injection pen according to the first exemplary embodiment of the present invention.

The exemplary embodiments described above may be provided as a reusable or disposable pen. In a disposable implementation, cartridge holder 14 and body 18 are preferably irreversibly assembled. In one embodiment, as described with respect to FIG. 3A, a circumferential rib provided on the cartridge holder 14 snaps into engagement with a groove 58 on body 18. In another embodiment, shown in FIG. 15A, threaded insert 114 may include at least one tab 125 for snap-fitting with a recess 126 provided on cartridge holder 114. Since threaded insert 114, as discussed with respect to FIGS. 11B and 11C, is fixed both axially and rotationally to body 18, snap-engagement of the cartridge holder 14 to threaded insert 114 prevents relative rotation between the cartridge holder and the body.

Figure 15B:
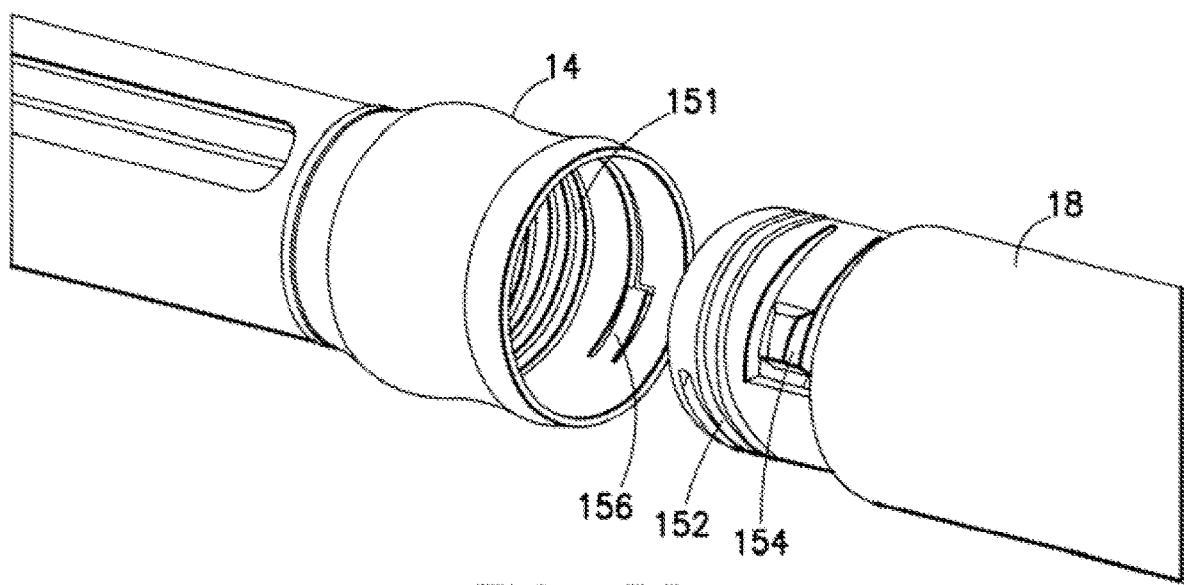

In a preferred embodiment shown in FIG. 15B, cartridge holder 14 and body 18 comprise a set of threads 151 and 152 which provide a secure threaded coupling between the cartridge holder 14 and body 18. Additionally, one of the cartridge holder and the body comprises a snap 154 and the other comprise a recess 156 for engaging snap 154. The snap/recess engagement is preferably a one-way radial snap. Thus, once the body 18 and the cartridge holder 14 are screwed together, the snap 154 moves into engagement with recess 156 until they snap together providing a secure, irreversible connection, with minimal or no play between the cartridge holder 14 and body 18 thereby increasing accuracy of the dose injection and reducing/eliminating unnecessary waste of medication.

Figure 16A:
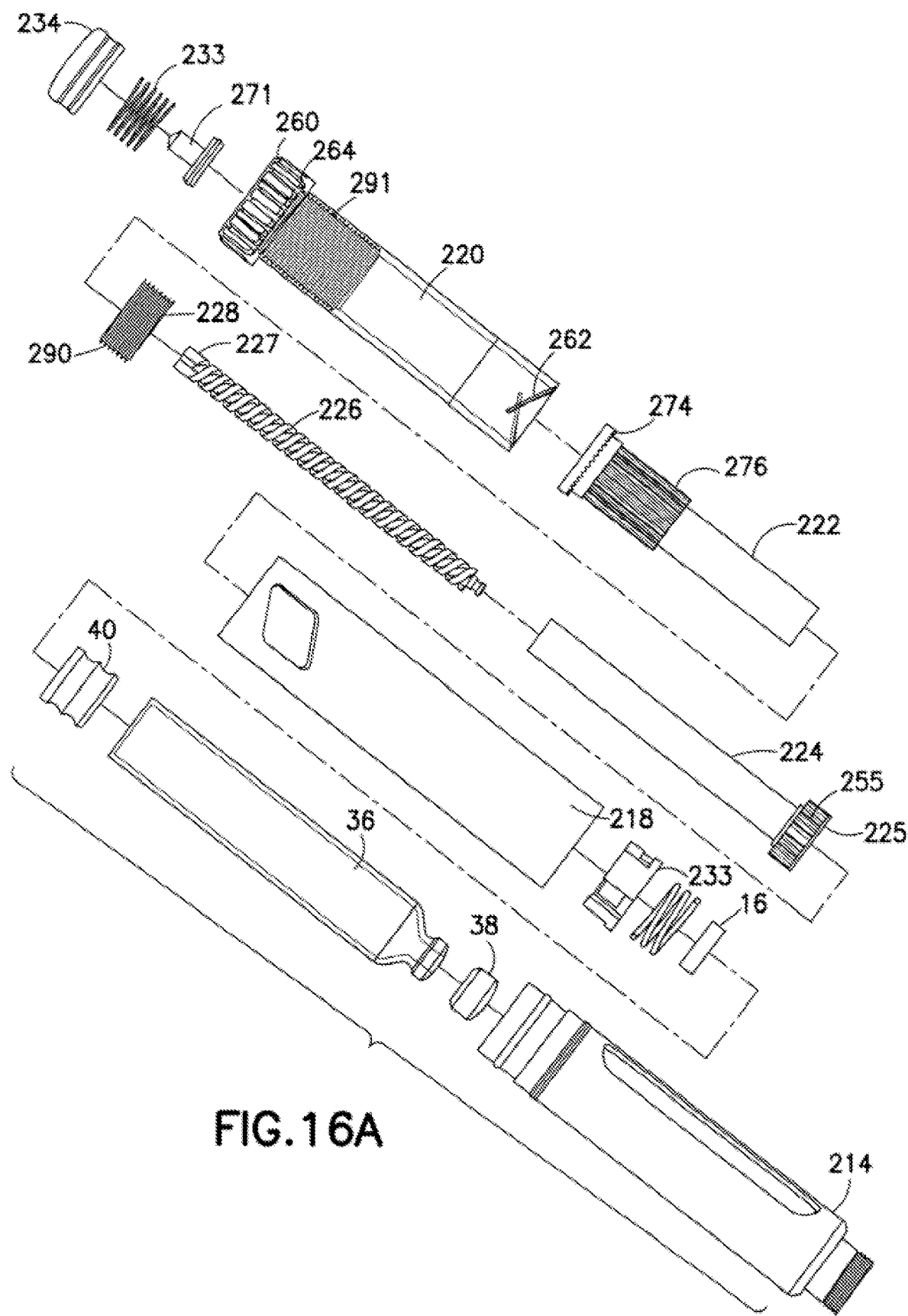
FIGS. 16A and 16B depict unassembled and assembled cross-sectional views, respectively, of exemplary components provided in a medication injection pen according to a second exemplary embodiment of the present invention.
Figure 16B:
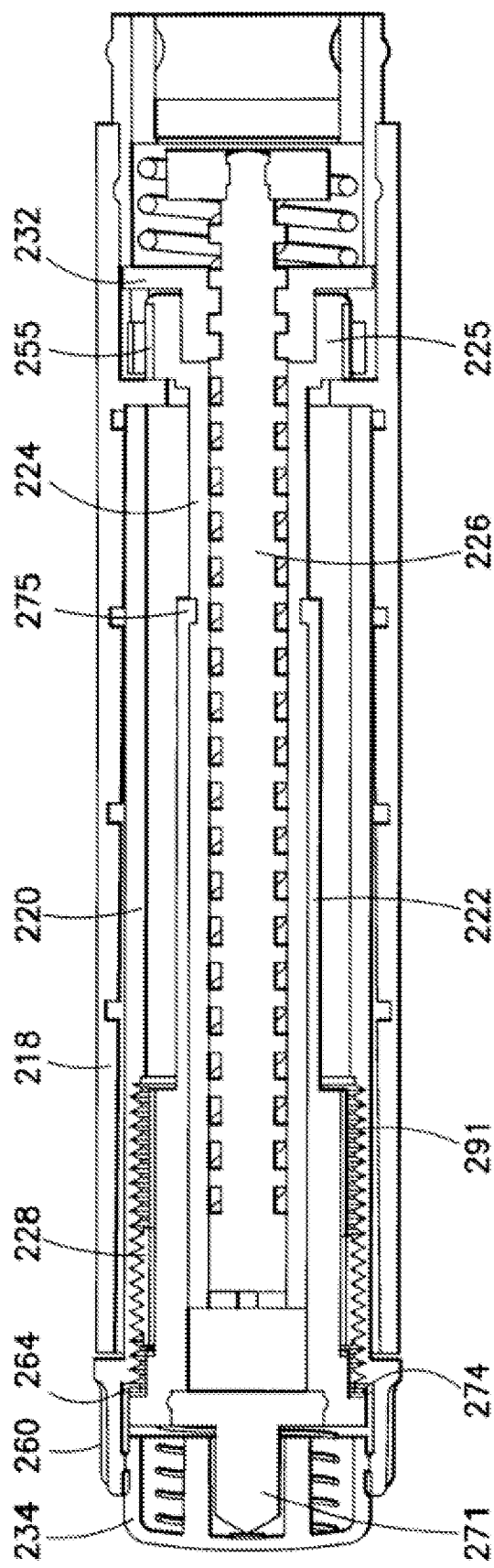

In view of the above description, another exemplary embodiment comprising similar components and functionality is shown in FIGS. 16A and 16B. The components shown in FIGS. 16A and 16B have similar functionality to those described above, unless noted otherwise, and therefore their detailed description is omitted herein. In this embodiment, body 218 is similar to the body 18" shown in FIGS. 11B and 11D. A first compartment defined by the interior of body 218, proximal to wall 250, houses a dose set knob 220, a setback member 222, a dose stop member 228, a driver 224, and a leadscrew 226. The second compartment defined by the interior of body 218, distal to wall 250, houses a threaded drive insert 233 and a distal end 225 of driver 224. Wall 250 is provided with an aperture sized to fit the main cylindrical body of driver 224, but not the enlarged distal end 225, as shown in FIG. 16B, thus axially fixing the driver 224 to the body 218.

Figure 17:
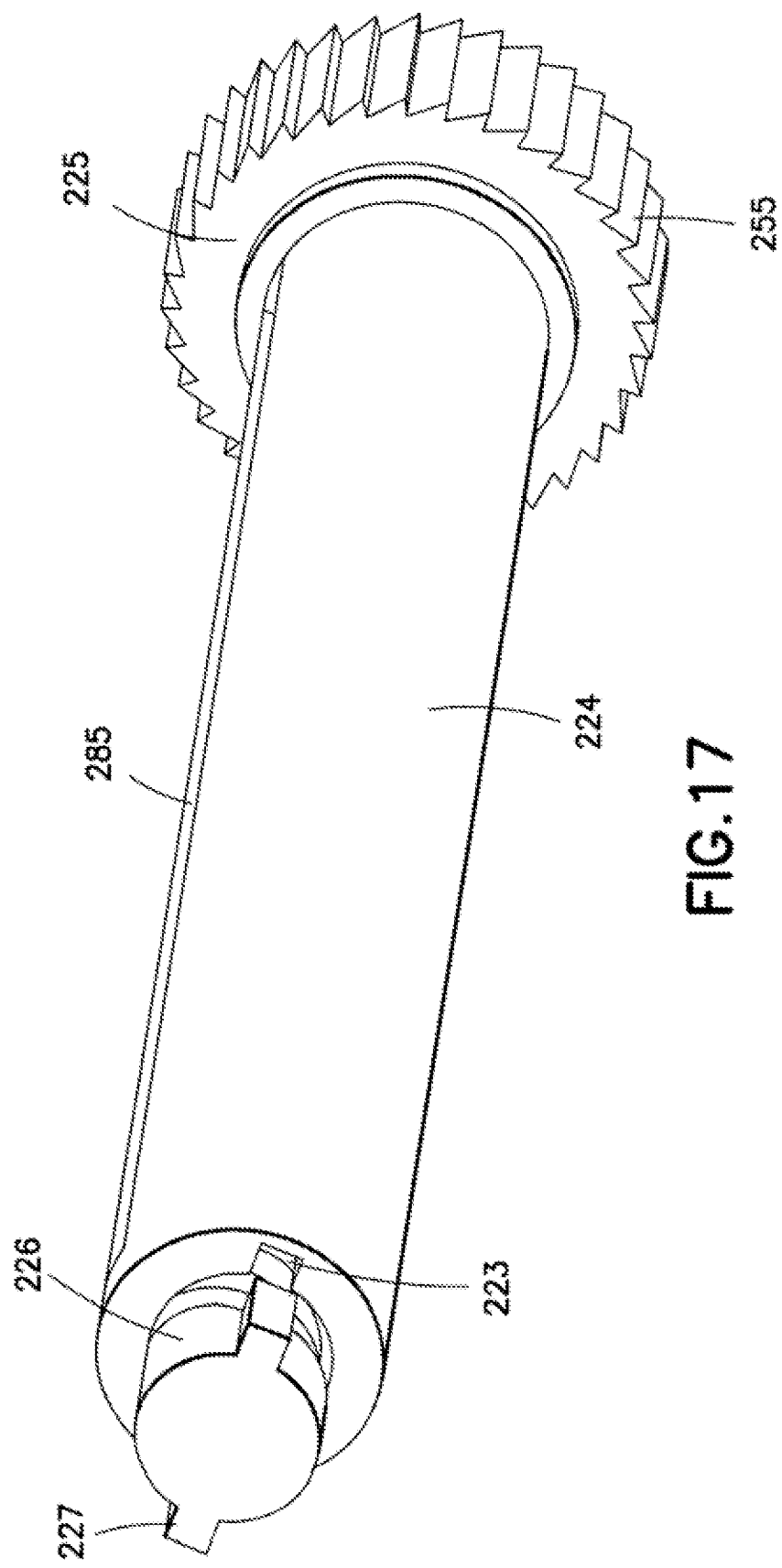
FIG. 17 depicts a view of a driver and leadscrew arrangement provided in a medication injection pen according to the second exemplary embodiment of the present invention.

In this embodiment, the leadscrew 226 has a circular cross-section, and is rotatably fixed to driver 224 via a key/groove engagement as shown in FIG. 17. A proximal end of leadscrew 226 includes keys 217 engaging in longitudinal grooves 223 provided on the interior of driver 224. Via this key/groove engagement, the leadscrew 226 is rotationally fixed to the driver 224 but is allowed to move axially relative thereto. Driver 224 comprises longitudinal grooves 285 engaging internal keys or splines 275 provided on the interior of setback member 222 to rotationally lock the driver 224 thereto. Driver 224 now includes an enlarged distal end 225 provided with a ring of teeth 255 circumferentially disposed thereon and functioning similarly to the toothed leadscrew brake 32' in FIGS. 11A and 11B. Distal end 225 comprises part of a unidirectional coupling along with the threaded insert 233, as similarly discussed above with respect to FIGS. 9B and 11B. Threaded insert 233 comprises an aperture with threads disposed thereon, which are threadedly coupled to corresponding threads on leadscrew 226, similar to insert 114 of FIG. 11C.

Figure 18:
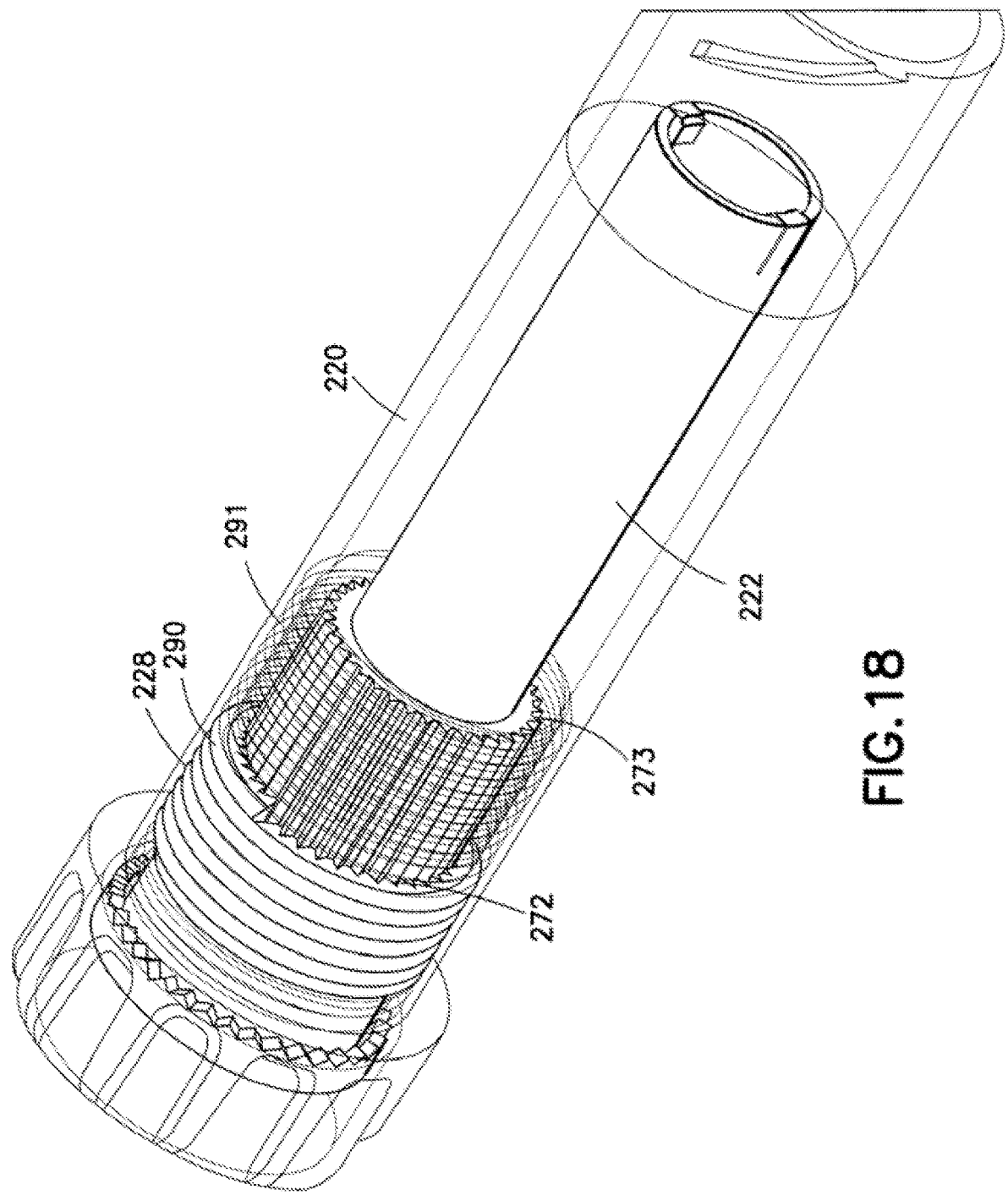
FIG. 18 depicts a view of a last dose control mechanism provided in a medication injection pen according to the second exemplary embodiment of the present invention.

In this embodiment, last dose control is provided by a modified dose stop member 228, as shown in FIG. 18. Dose stop member 228 comprises a ring link structure provided with a series of threads 290 disposed on the exterior surface thereof and threadedly engaged to threads 291 disposed on the dose set knob 220. Dose stop member 228 is rotationally fixed to setback member 222 via corresponding ridges 272 provided on the interior surface of dose stop member 228, which mesh with similar ridges 273 disposed on the setback member, as shown. In this embodiment, as the dose set knob 220 is rotated to set a desired dose or decrease a too-large dose, dose stop member 228 screws into threads 291 disposed on the dose set knob by an amount related to the set dose. During injection, the dose stop member 228 maintains its relative position with respect to threads 291, since the setback member 228 is rotationally fixed to the dose set knob 220. Therefore, dose stop member 228 and dose set knob 220 rotate together and there is no relative movement therebetween. Once the dose stop member 228 screws into the end thread of the threads 291, it is prevented from rotating further, and thus further rotation of the dose set knob to set a larger dose is also prevented. Such an occurrence indicates a Final dose of medication remaining in the cartridge.

To set a desired dose for injection the user rotates the dose set knob 220. Audible clicking of the set dose is provided by slipping of teeth 264 on dose set knob 220 with teeth 274 on setback member 222, as similarly described in the previous embodiment above. Teeth 264 and 274 are held in meshed engagement by a spring element 233 provided within push button 234. Similar to the previous embodiment, when the user presses push button 234 to inject a dose, the setback member 222 is rotationally locked to the dose set knob 220 via engagement between the teeth 264 and 274. Setback member 222 now rotates with dose set knob 220, as the dose set knob screws back into body 218. Rotation of the setback member 222 translates to driver 224 which rotates the leadscrew 226. The leadscrew 224 rotates through the fixed threaded drive insert 233 and into the cartridge to expel a dose. As the driver 225 rotates in this direction, the distal ring of teeth 255 provides the injection clicking as teeth 255 slip past ratchet arms disposed on threaded drive insert 233.

Figure 19A:
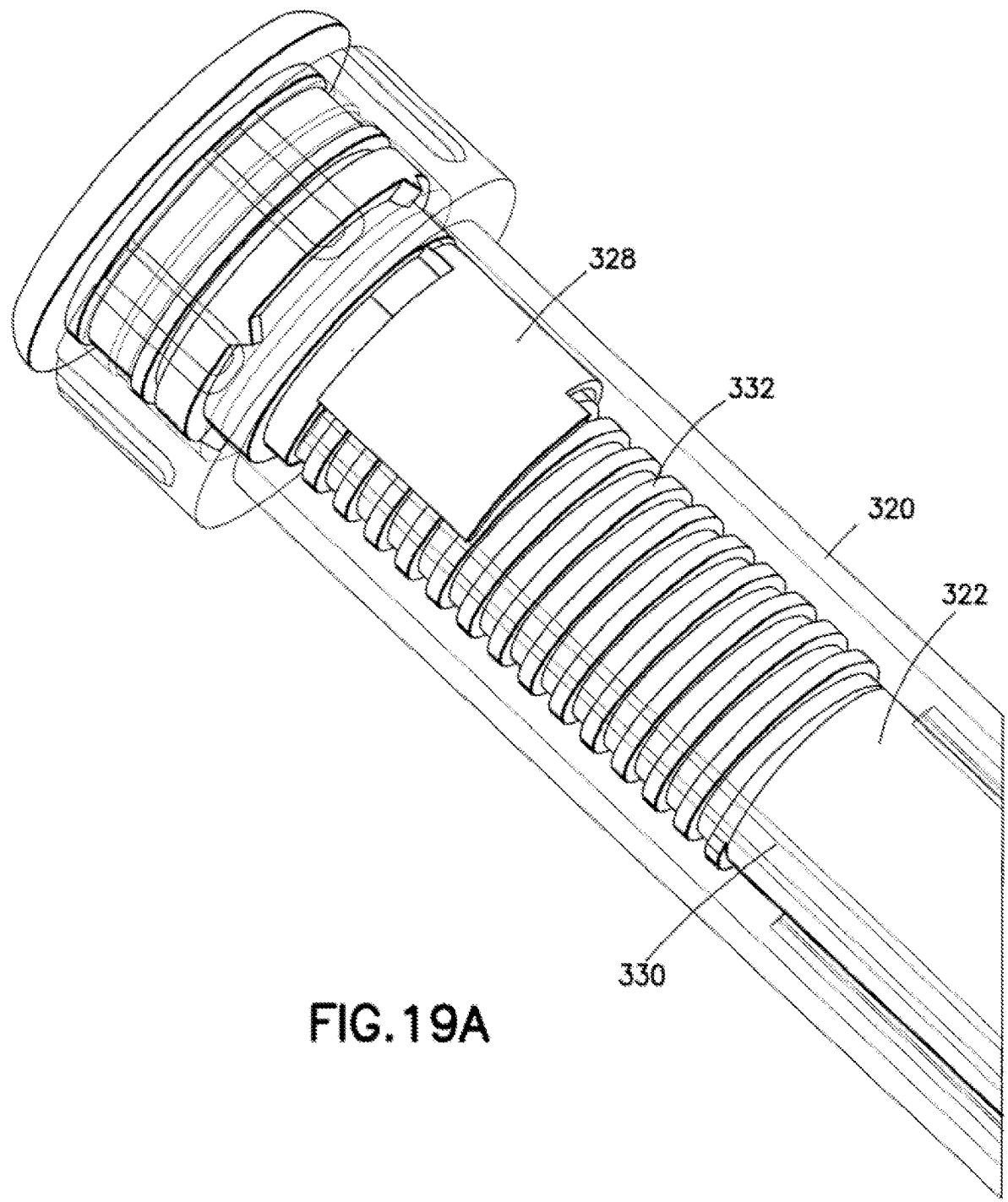
FIGS. 19A and 19B depict views of alternative last dose control mechanisms provided in a medication injection pen according to the second exemplary embodiment of the present invention.

In another embodiment, last dose control is similarly provided with a modified dose stop element 328, as shown in FIG. 19A. Dose stop element 328 is a half-nut like member with a series of threads disposed on the internal surface thereof, threadedly engaging threads 332 provided on threaded setback member 322. Dose set knob 320 comprises two longitudinally extending ribs or splines 330, circumferentially spaced from each other by a distance substantially the same as the length of the dose stop element 328, Splines 330 engage corresponding edges of dose stop element 328 to rotationally lock the dose stop element to the dose set knob 320. During setting of a dose, dose stop member 328 screws onto threads 332 of setback member 322, its relative position indicated the remaining volume of medication in the cartridge. When the dose stop member 328 reaches an end of thread 332 or a fixed stop on either the dose set knob 320 or setback member 322, dose stop element 328 is prevented from rotating further and thus limiting the dose to that remaining in the cartridge.

Figure 19B:
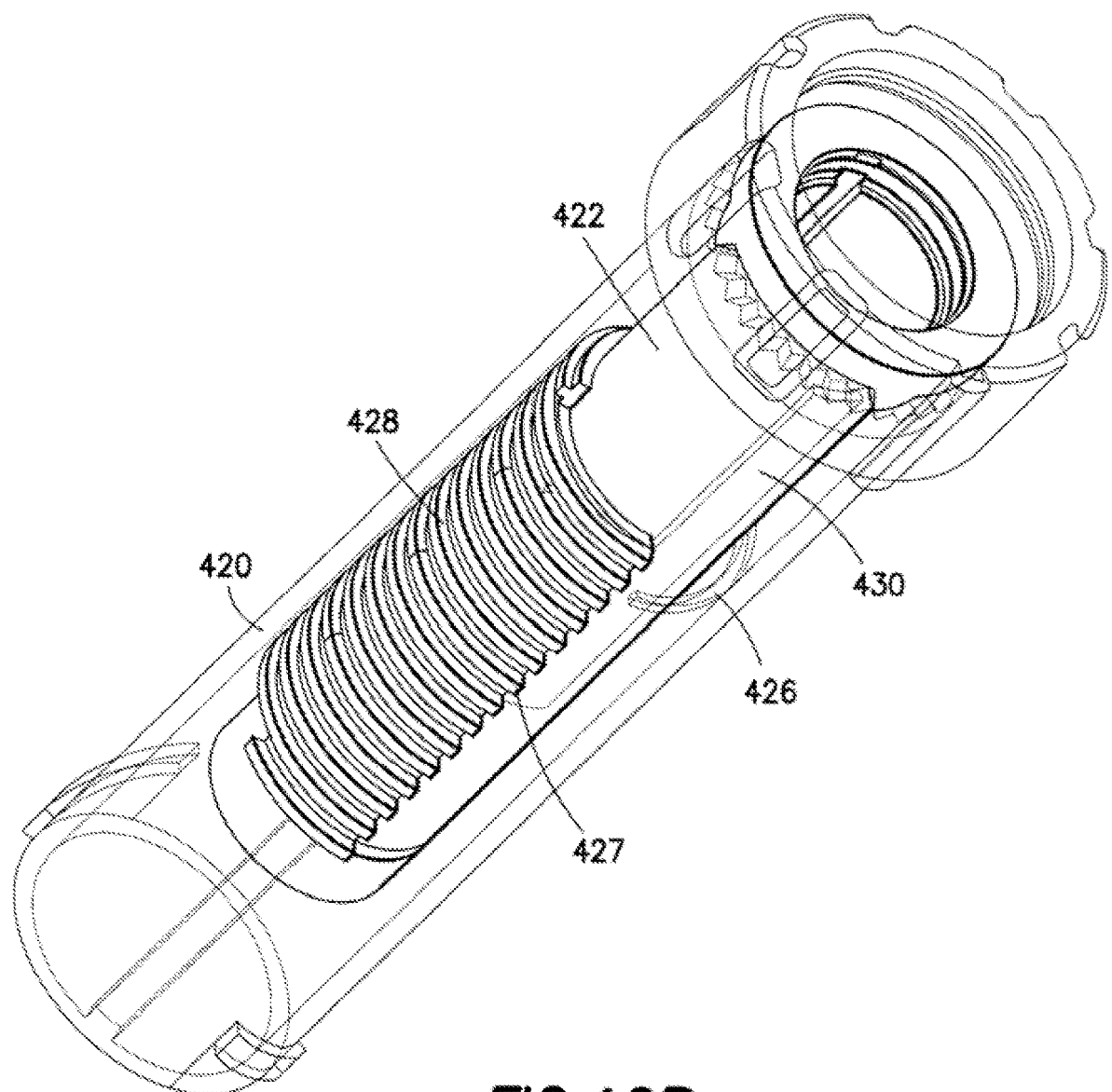

Yet another embodiment, using a similar principle of operation, is shown in FIG. 19B. In this embodiment, dose stop element 428 is threaded along its outer surface with threads 427. The inner surface of dose set knob 420 is provided with at least one thread disposed thereon with a length sufficient to maintain constant engagement with threads 427 of dose stop member 428. Setback member 422 comprises two longitudinally extending ribs or splines 430, circumferentially spaced from each other by a distance substantially the same as the length of the dose stop element 428. Splines 430 engage corresponding edges of dose stop element 428 to rotationally lock the dose stop element to the setback member 422. The outer surface of the setback member 422 in this embodiment is provided with a substantially smooth surface to enable axial movement of dose stop element 428 thereon. In this embodiment, the last dose volume is that indicated when dose stop element 428 is prevented from moving any farther axially with respect to setback member 422. Axial movement of dose stop element 428 is prevented when a first edge of element 428 abuts a fixed stop in the dose set knob 420 or on the setback member 422.

Figure 20:
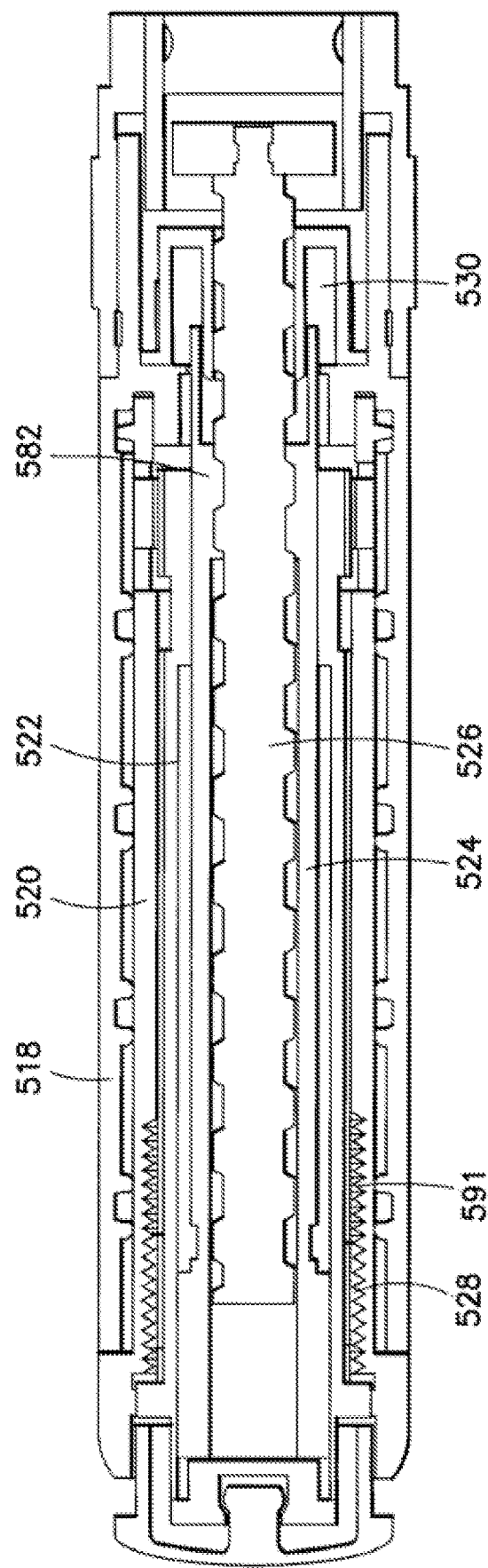
FIG. 20 depicts an assembled cross-sectional view of exemplary components provided in a medication injection pen according to a third exemplary embodiment of the present invention.
Figure 21:
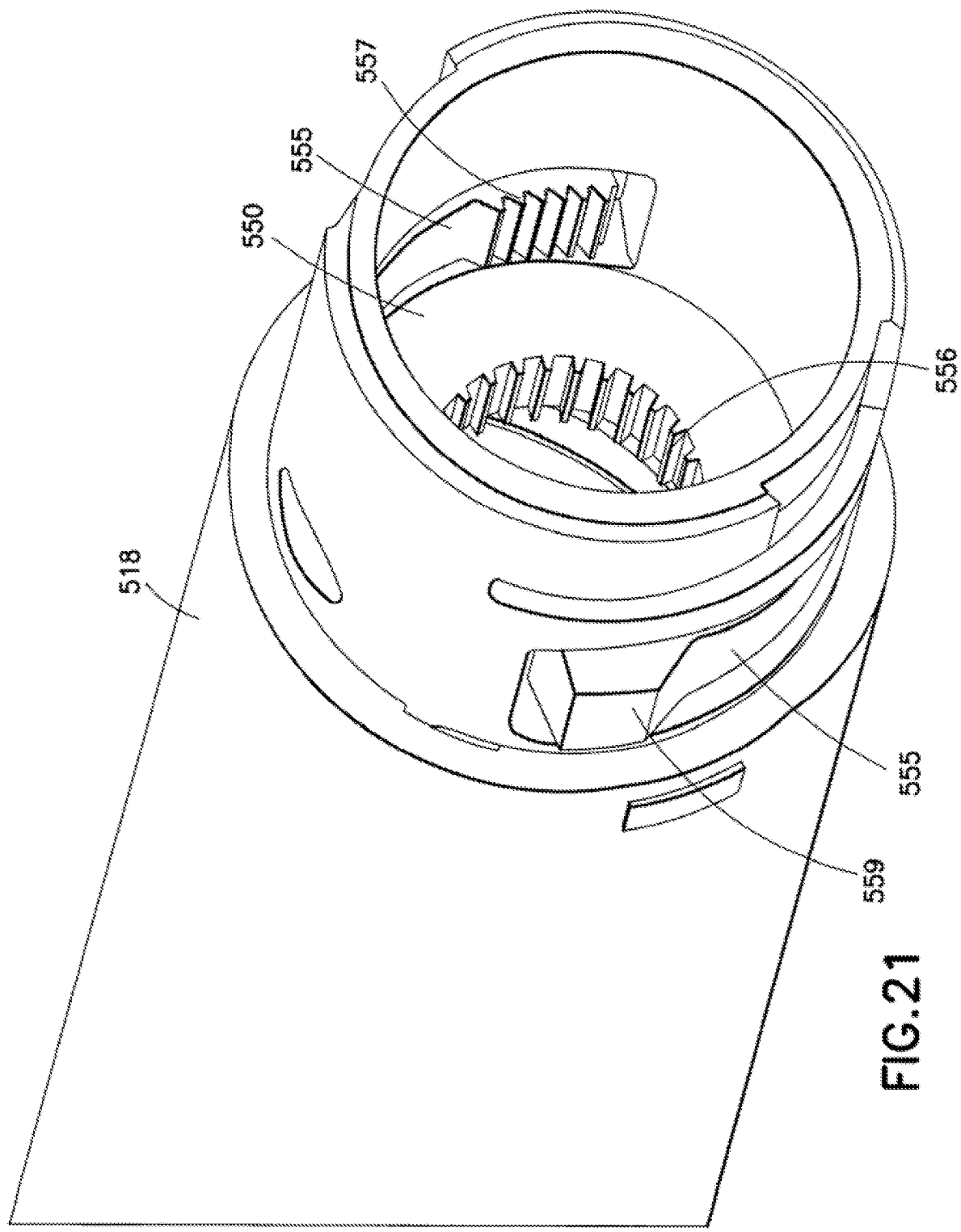
FIG. 21 depicts a view of a body provided in a medication injection pen according to the third exemplary embodiment of the present invention.
Figure 22:
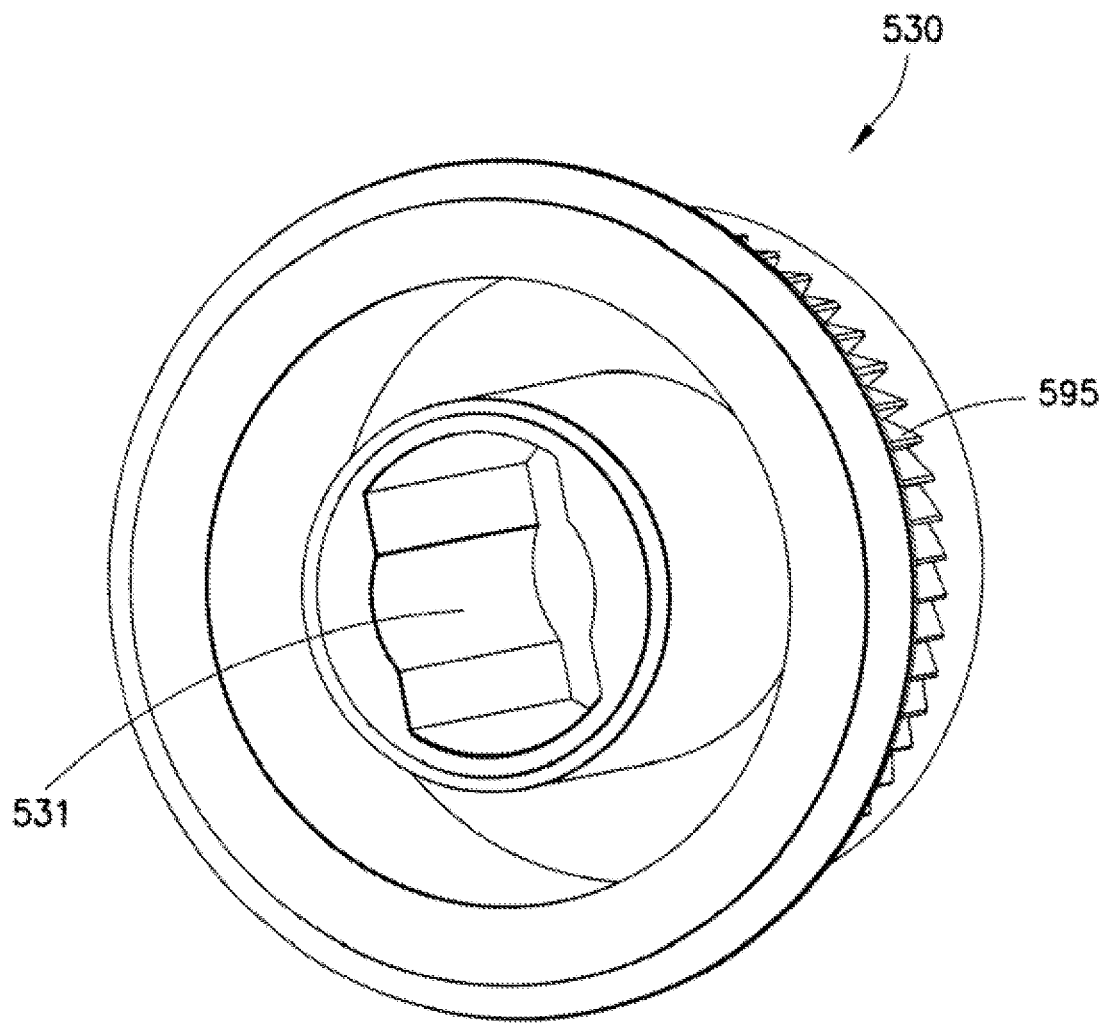
FIG. 22 depicts a view of an insert provided in a medication injection pen according to the third exemplary embodiment of the present invention.

In view of the above description, yet another exemplary embodiment of an injection pen comprising similar functionality is shown in FIG. 20. As shown in the cross-sectional view, an exemplary injection pen in this embodiment comprises a main body 518, a dose set knob 520, a setback member 522, a driver 524, a leadscrew 526, a dose stop member 528, and an insert 530. The body 518 is modified as shown in FIG. 21. As shown, at least one ratchet arm 555, attached at one end of a sidewall of the body 18 distal to the partition wall 550, is internally directed and preferably provided with series of ridges or teeth 557 at the free end thereof. Teeth 557 engage with teeth 595 disposed on the outer surface of insert 530, as shown in FIG. 22. Teeth 557 are forced into engagement with teeth 595 on the insert 530 when a cartridge holder is attached to body 18, due to the cartridge holder engaging protrusion 559 provided on the outer surface of ratchet arm 555. When the cartridge holder is attached to the body 518, the insert 530 is prevented from rotating in either direction due to the forced toothed engagement. When the cartridge holder is removed, such as to re-use the injection pen, the ratchet arms 555 are free to ratchet and enable relative rotation between the insert 530 and the body 518, to reload the leadscrew for subsequent use of the injection pen. The insert 530 comprises an aperture 531 with a non-circular cross-section for mating a similar non-circular cross-section of the leadscrew, to prevent relative rotation therebetween. A plurality of teeth 556 are provided circumferentially along an internal surface of the body 518 proximal to the partitioning wall 550. Teeth 556 serve to engage a ratchet element 586 provided near a distal end of driver 524, as shown in FIG. 23, described further below.

Figure 23:
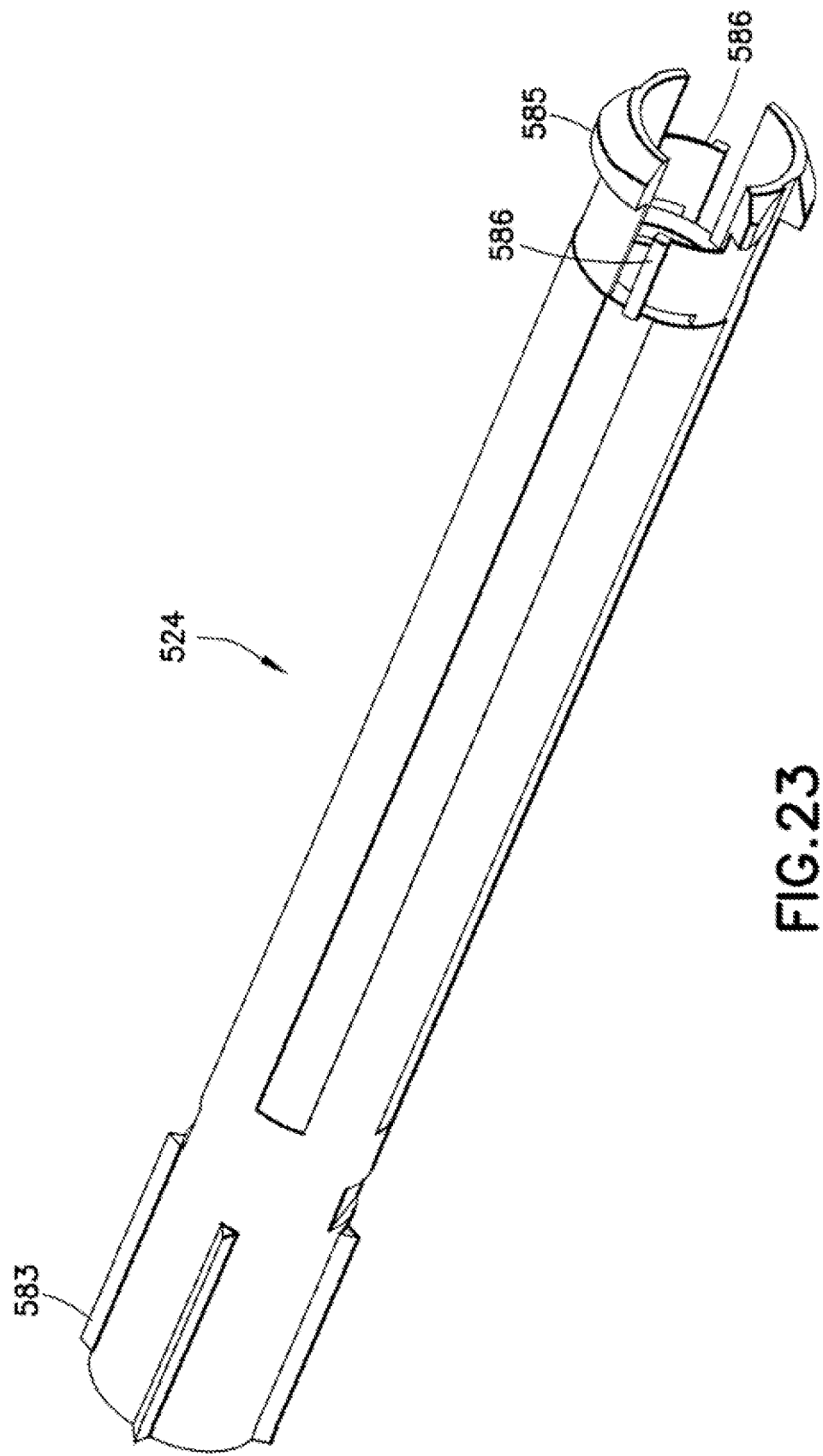
FIG. 23 depicts a view of a driver provided in a medication injection pen according to the third exemplary embodiment of the present invention.

As shown in FIG. 23, driver 524 comprises an elongated cylindrical member with open distal and proximal ends for allowing passage of the leadscrew 526 therethrough. Driver 524 includes a plurality of splines 583 provided near the proximal end for engaging corresponding grooves on the interior of setback member 522 for rotationally coupling the driver 524 and setback member 522 together. A pair of protrusions 585 is provided near the distal end of driver 524 for snap-engaging with the body 518 behind partitioning wall 550. This snap-engagement prohibits relative axial movement between the driver 524 and the body 518 while allowing relative rotational movement therebetween. Driver 524 includes at least one thread element 582 provided on the interior surface for threadedly engaging with a corresponding thread of the leadscrew 526. As discussed further below, it is this thread engagement that forces the leadscrew 526 to move axially in the distal direction to inject a set dose.

As shown in FIG. 24, the dose set knob 520 is an elongated cylindrical member provided with an outer thread 562 threadedly engaging an internal thread of the dose set knob, similar to the above embodiments. In this embodiment, the dose set knob 520 comprises at least one ratchet arm 564 provided near the distal end thereof, for engaging a plurality of ridges 573 provided on the outer surface of the setback member 522, as shown in FIG. 25. The ratchet arm 564 includes a rounded protrusion 565 for enabling slipping of the ratchet element in both directions over ridges 573 provided on setback member 522, to provide audible click signals during both normal dose setting and dial-back. Dose set knob 520 also includes a plurality of teeth 563 provided circumferentially along an internal surface of the dose set knob, as shown. During dose setting, teeth 563 are situated in the recess 576 on the outer surface of the setback member, as shown in FIG. 25. The teeth 563, in this embodiment, serve as an injection coupling to rotationally lock the dose set knob 520 to the setback member 522. In another embodiment, the injection coupling may be between a set of engaging teeth provided on the setback member 522 and the dose set knob 520, as similarly discussed with respect to the first embodiment shown in FIGS. 4A and 5A (teeth 64 and 74). Dose set knob 520 comprises a plurality of threads 591 provided along the internal surface thereof for threadedly engaging with threads 590 of the dose stop member 528.

Having described exemplary structures, features and interrelationships between the particular elements of FIGS. 20-25, the intended functionality of such an exemplary injection pen will now be described. Discussion of particular elements and features similar to the above embodiments, have been omitted herein.

To set a desired dose for injection, a user rotates the dose set knob 520 in a first direction. Relative rotation between the dose set knob 520 and the setback member 522 produces a series of dose-setting clicks due to the engagement between ridges 573 and ratchet elements 564, 565. If a too-large dose is set by the user, the user can rotate the dose set knob 520 in a second, opposite direction to dial back the set dose. During dose setting, the dose set knob is free to rotate in both the first and second direction with respect to the setback member 522. To inject a set dose, the user presses a push button 34, which pushes the setback member 522 in the distal direction and causes ridges 573 on the setback member to engage teeth 563 provided on the dose set knob. The dose set knob 520 and the setback member 522 are now rotationally fixed with respect to each other. Now, as the dose set knob rotates back into the body 518, the setback member 522 is also caused to rotate which forces driver 524 to rotate therewith. The leadscrew is prevented from rotating with respect to body 518 due to its mating engagement with the insert 530, which is rotationally fixed to the body 518 when the cartridge holder is attached to the body 518, as described above. Since the leadscrew 526 is rotationally fixed, relative rotation between the driver 524 and the leadscrew 526 causes the leadscrew 526 to move axially into the cartridge to inject a set dose, due to its threaded engagement with threads 582 provided on the driver 524. During injection, as the driver 524 rotates relative to body 518, ratchet arms 586 provide an injection click signal as they ride over teeth 556 provided on the interior of body 518. In this embodiment, last dose control is performed similarly to that described above with respect to FIG. 18, to prevent a user from setting a dose larger than a remaining volume of medication remaining in the cartridge.

While the present invention has been shown and described with reference to particular illustrative embodiments, it is not to be restricted by the exemplary embodiments but only by the appended claims and their equivalents. It is to be appreciated that those skilled in the art can change or modify the exemplary embodiments without departing from the scope and spirit of the present invention.

What is claimed is:
1. A medication injection pen comprising:
a housing;
a dose set knob comprising at least one internal thread and being rotatable with respect to said housing to set a desired injection dose;
a leadscrew provided with a thread element and advanceable is a first axial direction, said first axial direction being that which expels a medication from a cartridge;
a driver rotatable in a first rotation direction to rotate said leadscrew and advance said leadscrew in said first axial direction;
a setback member rotationally fixed to said driver for preventing relative rotation therebetween; and
a dose stop member rotationally fixed to said setback member and comprising an external thread in threaded engagement with said at least one internal thread of said dose set knob, said dose stop member being a unitary member axially movable relative to said dose set knob when said dose set knob is rotated relative to said setback member,
wherein axial movement of said dose stop member limits setting of the desired injection dose that is greater than an injectable volume of medication remaining in the cartridge.
2. The medication injection pen according to claim 1, wherein said dose stop member is rotationally coupled to the setback member between a pair of longitudinally extending ribs provided on said setback member.
3. The medication injection pen according to claim 2, wherein said dose stop member comprises a partial nut situated on said setback member between said longitudinally extending ribs.
4. The medication injection pen according to claim 3, wherein the axial movement of said dose stop member is limited when a first edge of the dose stop member abuts a fixed stop on said dose set knob or on said setback member.
5. The medication injection pen according to claim 2, wherein the axial movement of said dose stop member is limited when a first edge of the dose stop member abuts a fixed stop on said dose set knob or on said setback member.
6. The medication injection pen according to claim 1, wherein said dose stop member is rotationally coupled to the setback member via engagement between corresponding ridges provided on an internal surface of said dose stop member and an external surface of said setback member.
7. The medication injection pen according to claim 6, wherein said dose stop member comprises a ring link structure situated on said setback member.
8. The medication injection pen according to claim 7, wherein the axial movement of said dose stop member is limited when a first edge of the dose stop member abuts a fixed stop on said dose set knob or on said setback member.
9. The medication injection pen according to claim 6, wherein the axial movement of said dose stop member is limited when a first edge of the dose stop member abuts a fixed stop on said dose set knob or on said setback member.
10. The medication injection pen according to claim 1, wherein the axial movement of said dose stop member is limited when a first edge of the dose stop member abuts a fixed stop on said dose set knob or on said setback member.

* * * * *